(12) United States Patent
Cassis et al.

(10) Patent No.: US 11,986,464 B2
(45) Date of Patent: May 21, 2024

(54) 5HT3R ANTAGONIST FOR USE IN TREATING ANEURYSMS AND CARDIOVASCULAR RISK

(71) Applicant: University of Kentucky Research Foundation, Lexington, KY (US)

(72) Inventors: Lisa Cassis, Nicholasville, KY (US); Sean Thatcher, Lexington, KY (US); Yasir Alsiraj, Lexington, KY (US); Mark Ensor, Lexington, KY (US); Eric Blalock, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 17/734,571

(22) Filed: May 2, 2022

(65) Prior Publication Data

US 2022/0347161 A1 Nov. 3, 2022

Related U.S. Application Data

(60) Provisional application No. 63/182,161, filed on Apr. 30, 2021.

(51) Int. Cl.
| | |
|---|---|
| *A61K 31/439* | (2006.01) |
| *A61K 31/40* | (2006.01) |
| *A61K 31/4178* | (2006.01) |
| *A61K 31/4184* | (2006.01) |
| *A61K 31/46* | (2006.01) |
| *A61P 3/06* | (2006.01) |
| *A61P 9/10* | (2006.01) |

(52) U.S. Cl.
CPC ........ *A61K 31/439* (2013.01); *A61K 31/4178* (2013.01); *A61K 31/4184* (2013.01); *A61K 31/46* (2013.01); *A61P 3/06* (2018.01); *A61P 9/10* (2018.01)

(58) Field of Classification Search
CPC .. A61K 31/4178; A61K 31/439; A61K 31/46; A61K 31/4184; A61K 31/40; A61P 3/06; A61P 9/10
USPC .................................................. 514/295, 411
See application file for complete search history.

(56) References Cited

U.S. PATENT DOCUMENTS 8,580,730 B2 * 11/2013 Chabbert .................. A61P 1/08
514/1

OTHER PUBLICATIONS

Walstab et al., "5-HT3 receptors: Role in disease and target of drugs", 2010, Pharmacology & Therapeutics, 128(1), pp. 146-169. (doi: 10.1016/j.pharmthera.20 10.07.001) (Year: 2010).*
Tina K. Machu, "Therapeutics of 5-HT 3 receptor antagonists: Current uses and future directions", 2011, Pharmacology & Therapeutics, 130(3), pp. 338-347. (doi: 10.1016/j.pharmthera.2011.02.003) (Year: 2011).*

\* cited by examiner

*Primary Examiner* — Raymond J Henley, III
(74) *Attorney, Agent, or Firm* — Stites & Harbison PLLC; Mandy Wilson Decker

(57) ABSTRACT

Methods of treating or reducing risk of aneurysm, reducing cardiovascular risk, reducing serum cholesterol, reducing serum triglycerides, and/or reducing atherosclerotic plague in a subject involve administering to the subject an effective amount of a 5HT$_3$R antagonist.

20 Claims, 28 Drawing Sheets

5HT3R ANTAGONIST FOR USE IN TREATING ANEURYSMS AND CARDIOVASCULAR RISK

RELATED APPLICATIONS

This application claims priority from U.S. Provisional Application Ser. No. 63/182,161 filed Apr. 30, 2021, the entire disclosure of which is incorporated herein by this reference.

GOVERNMENT INTEREST

This invention was made with government support under grant number HL107326 awarded by the National Institutes of Health. The government has certain rights in the invention.

TECHNICAL FIELD

The presently-disclosed subject matter generally relates to methods of reducing cardiovascular risk, and methods of treating or reducing the risk of developing aneurysm, hypercholesterolemia, hypertriglyceridemia, and atherosclerosis. In particular, certain embodiments of the presently-disclosed subject matter relate to methods involving administration of a 5-hydroxytryptamine (serotonin) 3-receptor ($5HT_3R$) antagonist to a subject in need of such prophylactic or therapeutic treatment.

INTRODUCTION

An aneurysm is an excessive localized enlargement in an artery, resulting from a weakening of the artery wall. Aneurysms can occur in arteries in different regions of the body and can have distinct contributing mechanisms, including genetic influences and non-genetic influences (e.g., environmental factors). According to the Centers for Disease Control and Prevention (CDC), aortic aneurysms were the cause of 9,923 deaths in the United States in 2018. About 58% of these deaths occur in men. A history of smoking is associated with about 75% of all abdominal aortic aneurysms.

Currently-available treatments for aneurysm include surgery, such as endovascular aneurysm repair (EVAR). When surgery is not possible, or the risks are sufficient to eliminate surgery as a viable option, treatment is typically limited to monitoring the condition and providing adjuvant pharmacologic therapy, for example, to lower blood pressure or blood cholesterol. There are currently no known primary pharmacologic treatments for aneurysms that occur in any region of the aorta.

Atherosclerosis is the thickening, hardening, and narrowing of an artery caused by the build-up of plaque (made up of fats, cholesterol, and other substances) on the arterial inner wall, resulting in a narrowing of the artery. Hypercholesterolemia is the presence of high levels of cholesterol in the blood. Heightened serum cholesterol levels, particularly non-high density lipoprotein (HDL) cholesterol and low density lipoprotein (LDL) cholesterol, are associated with an increased risk of atherosclerosis and coronary heart disease. Hypertriglyceridemia is the presence of high amounts of triglycerides in the blood. High triglyceride levels are associated with atherosclerosis, even in the absence of hypercholesterolemia, and are associated with an increased risk of disease.

Despite a call for healthy lifestyle changes, as well as currently-available treatments, atherosclerosis remains the underlying cause of about 50% of all deaths in westernized society.[163]

Accordingly, there is a need in the art for effective prophylactic and therapeutic treatments for aneurysms, hypercholesterolemia, hypertriglyceridemia, and atherosclerosis.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature (s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes methods of treating or reducing risk of aneurysm, reducing cardiovascular risk, reducing serum cholesterol, reducing serum triglycerides, and reducing atherosclerotic plague in a subject, which involve administering to the subject an effective amount of a 5-hydroxytryptamine (serotonin) 3-receptor ($5HT_3R$) antagonist.

Some embodiments of the presently-disclosed subject matter include a method of treating or reducing risk of aneurysm in a subject in need thereof, which comprises administering to the subject an effective amount of a 5HT3R antagonist or pharmaceutically-acceptable salt thereof.

In some embodiments of the method, the subject is identified as having an aneurysm. In some embodiments, the subject is identified as being at risk of aneurysm. In some embodiments of the method, administration to the subject can result in a reduction in pathology, a reduction in the internal diameter of the aorta, a protection from an increase in internal diameter of the aorta, a reduction in the external diameter of the aorta, a protection from an increase in the external diameter of the aorta, a reduction in the incidence of aneurysm, or a protection from aneurysm.

In some embodiments of the method, the subject is identified as having particular risk factors. In some embodiments the subject is has a history of nicotine use. In some embodiments the subject is identified as having hypercholesterolemia. In some embodiments the subject is identified as having hypertriglyceridemia. In some embodiments the subject is identified as having atherosclerotic plague. In some embodiments, the subject is male or lacks two X chromosomes.

Some embodiments of the presently-disclosed subject matter include a method of treating hypercholesterolemia in a subject in need thereof, which comprises administering to the subject an effective amount of a 5HT3R antagonist or pharmaceutically-acceptable salt thereof. Some embodiments of the presently-disclosed subject matter include a method of reducing serum cholesterol levels in a subject in need thereof, which comprises administering to the subject an effective amount of a 5HT3R antagonist or pharmaceutically-acceptable salt thereof. In some embodiments of the method, the subject has a history of nicotine use or smoking. In some embodiments, the subject is identified as having a nicotine-induced cardiovascular risk. In some embodiments of the method, the subject is identified as being at risk of aneurysm. In some embodiments of the method, the subject is identified as having an aneurysm. In some embodiments of the method, the subject has elevated levels of cholesterol in the blood or serum, as determined by one skilled in the art. In some embodiments of the method, administration to the subject can result in reduced levels of serum cholesterol.

Some embodiments of the presently-disclosed subject matter include a method of treating hypertriglyceridemia in a subject in need thereof, which comprises administering to the subject an effective amount of a 5HT3R antagonist or pharmaceutically-acceptable salt thereof. Some embodiments of the presently-disclosed subject matter include a method of reducing serum triglyceride levels in a subject in need thereof, which comprises administering to the subject an effective amount of a 5HT3R antagonist or pharmaceutically-acceptable salt thereof. In some embodiments of the method, the subject has a history of nicotine use or smoking. In some embodiments, the subject is identified as having a nicotine-induced cardiovascular risk. In some embodiments of the method, the subject is identified as being at risk of aneurysm. In some embodiments of the method, the subject is identified as having an aneurysm. In some embodiments of the method, the subject has elevated levels of triglycerides in the blood or serum, as determined by one skilled in the art. In some embodiments of the method, administration to the subject can result in reduced levels of serum triglycerides cholesterol.

Some embodiments of the presently-disclosed subject matter include a method of reducing atherosclerotic plague in a subject in need thereof, which comprises administering to the subject an effective amount of a 5HT3R antagonist or pharmaceutically-acceptable salt thereof. In some embodiments of the method, the subject has a history of nicotine use or smoking. In some embodiments, the subject is identified as having a nicotine-induced cardiovascular risk. In some embodiments of the method, the subject is identified as being at risk of aneurysm. In some embodiments of the method, the subject is identified as having an aneurysm. In some embodiments of the method, atherosclerotic plague has been detected in the subject. In some embodiments of the method, administration to the subject can result in a reduction in atherosclerotic plague.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 2A. The percentage of mice of each genotype with DTA pathology. FIG. 2B. Aortas from mice of each group. To the right are larger images of DTA from 2 mice/group. Boxes represent aortas illustrated at larger sizes. Data are mean±SEM from n=10-15/group. *, $P<0.05$ compared to XXF or XYM within sex. **, $P<0.05$ compared to XXF.

FIG. 5A. The percentage of mice of each genotype with AA pathology. FIG. 5B. Aortas from mice of each group. Data are mean±SEM from n=10-15/group. *, $P<0.05$ compared to XXF or XYM within sex. **, $P<0.05$ compared to XXF.

FIG. 12A. Percent of mice with AA pathology. FIG. 12B. Thoracic aortic weights. FIG. 12C. Representative in situ aorta from each group. Data are mean±SEM from n=10-15 mice/group. *, $P<0.05$ compared to AngII within sex.

FIG. 21A. Systolic blood pressures. FIG. 21B. Diastolic blood pressures. *P<0.05 compared to AngII.

DESCRIPTION OF EXEMPLARY EMBODIMENTS

Figure 1:
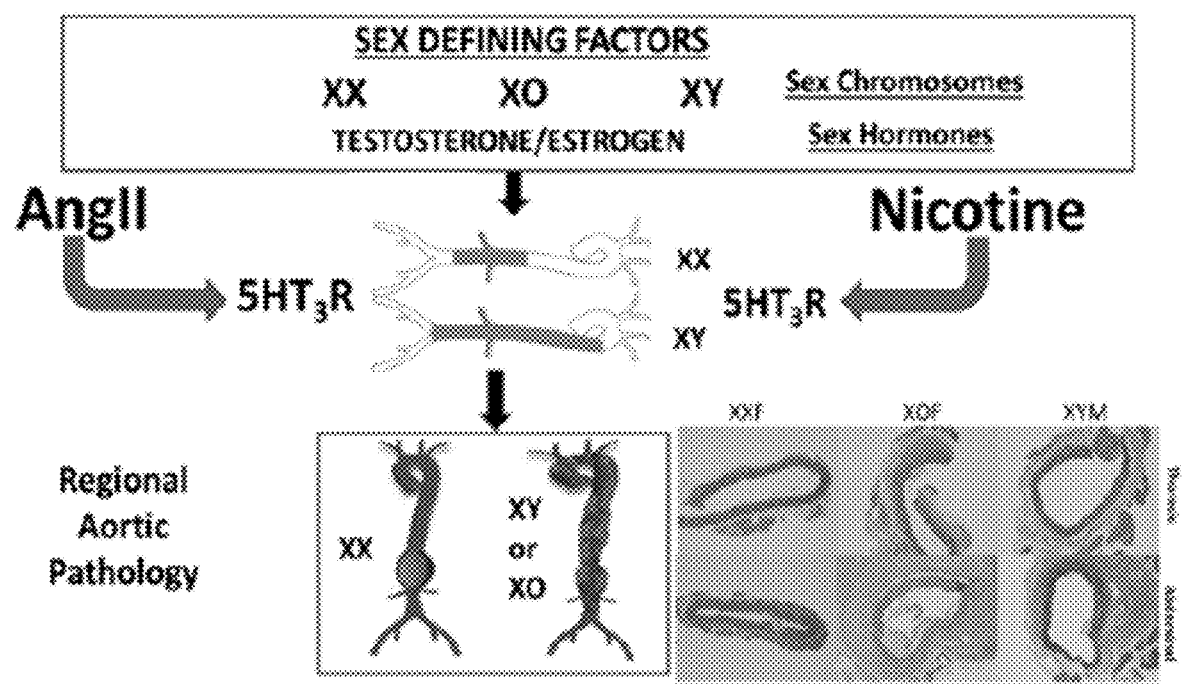
FIG. 1. Schematic illustration of angiotensin II (AngII) invoking a 5HT3R driven mechanism to promote sexually dimorphic aortic pathology in a regional-specific matter, with effects augmented by nicotine, a well-known risk factor and initiator of aortic pathology.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes methods of treating or reducing risk of aneurysm, reducing cardiovascular risk, reducing serum cholesterol, reducing serum triglycerides, and reducing atherosclerotic plaque in a subject, which involve administering to the subject an effective amount of a 5-hydroxytryptamine (serotonin) 3-receptor ($5HT_3R$) antagonist.

5-Hydroxytryptamine (Serotonin) 3-Receptor ($5HT_3R$) Antagonist

There are a number of antagonists of $5HT_3R$ known in the art.[158] $5HT_3R$ antagonists have been used clinically to treat irritable bowel syndrome.[93] Other uses of $5HT_3R$ antagonists include the treatment of chemotherapy-induced nausea and vomiting[158], anxiety and depression, schizophrenia, substance use disorders, and use as analgesics or anti-inflammatory agents.[83] To date, the potential clinical utility of $5HT_3R$ antagonists in the realm of cardiovascular diseases is largely unknown, despite the initial discovery of 5HT as a potent vasoconstrictor. Indeed, prior to the disclosure herein, there has been no teaching or suggestion for the use of $5HT_3R$ antagonists in methods of reducing cardiovascular risk, or in methods of treating or reducing the risk of developing aneurysm, aortopathy, hypercholesterolemia, hypertriglyceridemia, and atherosclerosis.

Any $5HT_3R$ antagonist can be selected for use in connection with the presently-disclosed subject matter. Examples of $5HT_3R$ antagonist that can be used include, but are not limited to, tropisetron ((1R,5S)-8-methyl-8-azabicyclo[3.2.1]octan-3-yl]1H-indole-3-carboxylate); dolasetron ((2α,6α,9αβ)-Octahydro-3-oxo-2,6-methano-2H-quinolizin-8-yl ester-1H-indole-3-carboxylic acid monomethanesulfonate); granisetron (endo-1-Methyl-N-(9-methyl-9-azabicyclo[3.3.1]non-3-yl)-1H-indazole-3-carboxamide monohydrochloride); ondansetron (1,2,3,9-Tetrahydro-9-methyl-3-[(2-methyl-1H-imidazol-1-yl)methyl]-4H-carbazol-4-one monohydrochloride dehydrate); palonosetron ((S)-2-[(3S)-Quinuclidin-3-yl]-2,3,3a,4,5,6-hexahydro-1H-benzo[de]isoquinolin-1-one hydrochloride): and ramosetron ((1-methylindol-3-yl)-[(5R)-4,5,6,7-tetrahydro-3H-benzimidazol-5-yl]methanone). In some embodiments, the methods disclosed herein involve administering two or more distinct $5HT_3R$ antagonists to a subject.

As will be appreciated by the skilled artisan, the $5HT_3R$ antagonist can be provided as a pharmaceutical salt of the $5HT_3R$ antagonist. As will also be appreciated by the skilled artisan, the $5HT_3R$ antagonist can be provided in a pharmaceutical composition. As will also be appreciated by the skilled artisan, the $5HT_3R$ antagonist, can be formulated in a manner appropriate for the desired mode of administration. Examples of appropriate modes of administration include, but are not limited to oral, intravenous, and subcutaneous.

Aneurysm

The presently-disclosed subject matter includes a method of treating or reducing risk of aneurysm in a subject in need thereof, which comprises administering to the subject an effective amount of a 5HT3R antagonist or pharmaceutically-acceptable salt thereof.

An aneurysm is an excessive localized enlargement in an artery, resulting from a weakening of the artery wall. Aneurysms can occur in arteries in different regions of the body. A cerebral aneurysm, also referred to as an intracranial aneurysm or a brain aneurysm occurs when the localized enlargement is in the brain. An aortic aneurysm occurs when the localized enlargement is in the aorta. Aortic aneurysms can occur in different regions of the aorta, for example, within the aortic arch, distal thoracic, or abdominal aorta. An abdominal aortic aneurysm (AAA) happens below the chest. Abdominal aortic aneurysms are more common than thoracic aortic aneurysms. Contributing risk factors for AAAs include smoking and male sex, with some studies suggesting associations of atherosclerosis or hypertension with AAA development and expansion.

Aneurysms can be diagnosed using various technology known in the art, which can be selected by one skilled in the art based on, for example, information specific to a particular subject and location in the body of the subject that is of particular interest. Such technology includes, for example, ultrasound, computerized tomography (CT) scan, magnetic resonance imaging (MRI), or angiogram.

One skilled in the art of clinically diagnosing aneurysms (such as, for example, a cardiologist, cardiothoracic surgeon, neurologist, neurosurgeon, radiologist, or other medical practitioner) can determine whether a localized enlargement in an artery is excessive, and therefore qualifies as an aneurysm. The size of an artery that is deemed by a skilled artisan to be excessively enlarged will depend on the particular subject being examined and the particular artery within the subject that is being examined. Examples of factors that may be relevant to the determination by the skilled artisan could include, but are not limited to, age, body weight, and sex of the subject. In some cases, for example, a localized enlargement to about 1.5 times or more of the artery's normal diameter can be considered an aneurysm. For another example, when considering the aorta, an internal diameter of 3 cm or more is often considered to be an aneurysm. For aortic aneurysms that are less than 5 cm, monitoring and non-surgical treatment is often recommended, and for aneurysms that are greater than 5 cm, repair is often recommended. Also, repair is often recommended when an aneurysm that is being monitored expands by more than about 0.6 cm per year. Accordingly, it can be determined by knowledge of one skilled in the art whether a particular subject is in need of treatment for or reduction of risk of aneurysm.

In some embodiments of the method, the subject is identified as having an aneurysm. In some embodiments, the subject is identified as being at risk of aneurysm. In some embodiments of the method, administration to the subject can result in a reduction in pathology, a reduction in the internal diameter of the aorta, a protection from an increase in internal diameter of the aorta, a reduction in the external diameter of the aorta, a protection from an increase in the external diameter of the aorta, a reduction in the incidence of aneurysm, or a protection from aneurysm.

In some embodiments of the method, the aneurysm is a cerebral aneurysm. In some embodiments, the aneurysm is an aortic aneurysm. The aortic aneurysms can be, for example, within the aortic arch, distal thoracic, or abdominal aorta. In some embodiments, the aortic aneurysm is an abdominal aortic aneurysm (AAA). In some embodiments, the aortic aneurysm is a thoracic aortic aneurysms.

In some embodiments of the method, the subject is identified as having particular risk factors. In some embodiments the subject is has a history of nicotine use. In some embodiments the subject is identified as having hypercholesterolemia. In some embodiments the subject is identified as having hypertriglyceridemia. In some embodiments the subject is identified as having atherosclerotic plaque. In some embodiments, the subject is male or lacks two X chromosomes.

Hypercholesterolemia, Hypertriglyceridemia, and Atherosclerosis

The presently-disclosed subject matter includes a method of reducing serum cholesterol in a subject, a method of reducing serum triglycerides in a subject, and a method of reducing atherosclerotic plaque in a subject, which comprise administering to the subject an effective amount of a 5HT3R antagonist or pharmaceutically-acceptable salt thereof.

Atherosclerosis is the thickening, hardening, and narrowing of an artery caused by the build-up of plaque (made up of fats, cholesterol, and other substances) on the arterial inner wall, resulting in a narrowing of the artery.

Hypercholesterolemia is the presence of high levels of cholesterol in the blood. Heightened serum cholesterol levels, particularly non-high density lipoprotein (HDL) cholesterol and low density lipoprotein (LDL) cholesterol, are associated with an increased risk of atherosclerosis. Hypertriglyceridemia is the presence of high amounts of triglycerides in the blood, which is associated with an increased risk of atherosclerosis.

It is has been suggested that atherosclerosis could initiate with injury to the inner wall of an artery, such that substances can accumulate at the site of the injury, and over time plaque builds up at the injury sight and hardens, narrowing the artery. In this regard, risk factors can include those that contribute to injuring the inner wall of an artery, as well as those that provide a source for components of plaque. Accordingly, examples of risk factures include, blood cholesterol levels, blood triglyceride levels, blood pressure, insulin resistance, diabetes status, body fat, alcohol consumption, nicotine consumption, and inflammation, such as including inflammation from a secondary condition such as arthritis, lupus, psoriasis, or inflammatory bowel disease.

Atherosclerosis can be diagnosed using various technology known in the art, which can be selected by one skilled in the art based on, for example, information specific to a particular subject and information specific to the location in the body of the subject. Such technology includes, for example, ultrasound, computerized tomography (CT) scan, CT angiopraphy, angiogram, blood pressure comparison, radionuclide angiography, echocardiogram, electrocardiogram (ECG or EKG), stress test, positron emission tomography (PET) scan, and myocardial perfusion imaging.

One skilled in the art of clinically diagnosing atherosclerosis (such as, for example, a cardiologist, cardiothoracic surgeon, neurologist, neurosurgeon, radiologist, or other medical practitioner) can determine whether conditions are present such that a particular subject is diagnosed with atherosclerosis, and whether atherosclerosis has persisted, increased, or decreased in a particular subject relative to a prior assessment of that subject. Accordingly, it can be determined by knowledge of one skilled in the art whether a particular subject is in need of is in need of treatment for or reduction of risk of artherosclerosis.

Hypercholesterolemia and hypertriglyceridemia can be assessed using known laboratory tests for assessing levels of cholesterol and triglycerides in the blood or serum of a subject. Accordingly, it can be determined by knowledge of one skilled in the art whether a particular subject is in need of is in need of treatment for or reduction of risk of hypercholesterolemia and/or hypertriglyceridemia.

In some embodiments of the method of reducing serum cholesterol, reducing serum triglycerides, and/or reducing atherosclerotic plaque, the subject has a history of nicotine use or smoking. In some embodiments, the subject is identified as having a nicotine-induced cardiovascular risk. In some embodiments of the method, the subject is identified as being at risk of aneurysm.

In some embodiments of the method, the subject is identified as having an aneurysm. In some embodiments of the method, the subject has elevated levels of cholesterol and triglycerides in the blood or serum, as determined by one skilled in the art. In some embodiments of the method, administration to the subject can result in reduced levels of serum cholesterol. In some embodiments of the method, administration to the subject can result in reduced levels of serum triglycerides.

In some embodiments of the method, atherosclerotic plaque has been detected in the subject. In some embodiments of the method, administration to the subject can result in a reduction in atherosclerotic plaque.

Cardiovascular Risk

The presently-disclosed subject matter includes a method of reducing cardiovascular risk in a subject in need thereof, which comprises administering to the subject an effective amount of a 5HT3R antagonist or pharmaceutically-acceptable salt thereof.

Cardiovascular risk is a probability of suffering a future clinical cardiovascular event or disease. Cardiovascular events or diseases include, for example, angina, myocardial infarction (MI) or heart attack, stroke, heart failure, hypertensive heart disease, rheumatic heart disease, coronary heart disease, cardiomyopathy, aortic aneurysms, peripheral artery disease, thromboembolic disease, and venous thrombosis. As will be appreciated by one skilled in the art, certain conditions can give rise to an increased risk of certain cardiovascular events or diseases. For example, a subject having an aneurysm, hypercholesterolemia, hypertriglyceridemia, and atherosclerosis can have an increased risk of an event such as a heart attack.

There are a number of cardiovascular risk factures, which include, for example, blood cholesterol levels, blood triglyceride levels, blood pressure, insulin resistance, diabetes status, body fat, physical activity, diet, alcohol consumption, and nicotine consumption. Indeed, nicotine consumption (smoking) is one of the most significant risk factors for a cardiovascular disease or event. Certain infections can also impact cardiovascular risk. In this regard, subjects with coronavirus disease (COVID) have increased cardiovascular risk. Indeed, COVID-19 patients having aortic aneurysm may be at a higher risk for enlargement and rupture.[161] On skilled in the art of assessing risk for a cardiovascular disease or event (such as, for example, a cardiologist, cardiothoracic surgeon, radiologist, or other medical practitioner) can determine whether sufficient factors are present to warrant intervention such as therapeutic and/or prophylactic treatment to reduce cardiovascular risk. Accordingly, it can be determined by knowledge of one skilled in the art whether a particular subject is in need of treatment for reducing cardiovascular risk.

In some embodiments of the method of reducing cardiovascular risk, the subject has a history of nicotine use or smoking. In some embodiments, the subject is identified has having nicotine-induced cardiovascular risk. In some embodiments of the method of reducing cardiovascular risk, the subject has been infected with a coronavirus or has COVID. In some embodiments of the method, the subject is identified as being at risk of aneurysm. In some embodiments of the method, the subject is identified as having an aneurysm. In some embodiments of the method, the subject is identified as having hypercholesterolemia. In some embodiments of the method, the subject is identified as having hypertriglyceridemia. In some embodiments of the method, the subject is identified as having atherosclerotic plague.

Definitions

While the terms used herein are believed to be well understood by those of ordinary skill in the art, certain definitions are set forth to facilitate explanation of the presently-disclosed subject matter.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "effective amount" refers to an amount that is sufficient to achieve the desired prophylactic or therapeutic result or to have an effect on undesired symptoms, but is generally insufficient to cause adverse side effects. The specific effective amount for any particular subject will depend upon a variety of factors including the particular risk or condition being treated and the severity of the condition; the specific composition employed; the age, body weight, general health, sex and diet of the subject; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual medical practitioner in the event of any contraindications. Dosage can vary, and can be administered in one or more dose administrations daily, for one or several days. Guidance can be found in the literature for appropriate dosages for given classes of compounds and products As used herein, "optional" or "optionally" means that the subsequently described event or circumstance does or does not occur and that the description includes instances where said event or circumstance occurs and instances where it does not. For example, a subject who optionally displays symptoms means that, in some instances the subject can display symptoms; in other words, it means that the subject displays symptoms or does not display symptoms.

The term "subject" when referring to a subject having a particular condition or risk thereof, or a subject in need treatment for a particular condition or risk thereof refer to a target of administration, which optionally displays symptoms and/or has risk factures related to the particular condition or risk thereof, as would be considered relevant to one skilled in the medical art of making a diagnosis of the particular condition or risk thereof. As used herein, the term "subject" can refer to a vertebrate, such as a mammal. The term includes human and veterinary subjects. Thus, the subject can be a human, non-human primate, horse, pig, rabbit, dog, sheep, goat, cow, cat, guinea pig, or rodent. The term does not denote a particular age or sex.

As used herein, the term "treatment" is inclusive of prophylactic treatment and therapeutic treatment. As would be recognized by one of ordinary skill in the art, treatment that is administered prior to clinical manifestation of a condition is prophylactic (i.e., it protects the subject against or reduces the risk of the subject developing the condition). If the treatment is administered after manifestation of the condition, the treatment is therapeutic (i.e., it is intended to diminish, ameliorate, control, or maintain the existing condition and/or side effects associated with the condition). The terms relate to medical management of a subject with the intent to substantially cure, ameliorate, stabilize, or substantially prevent a condition of interest (e.g., disease, pathological condition, or disorder), including but not limited to prophylactic treatment to preclude, avert, obviate, forestall, stop, or hinder something from happening, or reduce the severity of something happening, especially by advance action. As such, the terms treatment or treating include, but are not limited to: inhibiting the progression of a condition of interest; arresting or preventing the development of a condition of interest; reducing the severity of a condition of interest; ameliorating or relieving symptoms associated with a condition of interest; causing a regression of the condition of interest or one or more of the symptoms associated with the condition of interest; and preventing a condition of interest or the development of a condition of interest. The terms includes active treatment, that is, treatment directed specifically toward the improvement of a condition of interest, and also includes causal treatment, that is, treatment directed toward removal of the cause of the condition of interest.

Unless defined otherwise, all technical and scientific terms used herein have the same meaning as is commonly understood by one of skill in the art to which the invention(s) belong.

All patents, patent applications, published applications and publications, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

EXAMPLES

The presently-disclosed subject matter is further illustrated by the following specific but non-limiting examples.

The following examples may include compilations of data that are representative of data gathered at various times during the course of development and experimentation related to the present invention.

Example 1: Descending Thoracic Aorta (DTA) Pathology

Figure 2A:
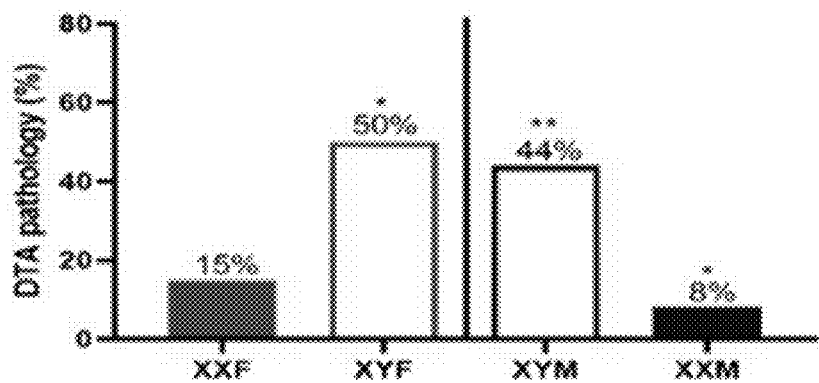
FIGS. 2A and 2B. AngII-induced descending thoracic aorta (DTA) pathology in Four Core Genotype XXF, XYF, XYM and XXM mice.

Aortic pathology in the descending thoracic aorta (DTA) was quantified as the percentage of mice that exhibit pathology (FIG. 2A). Female (XXF) mice infused with AngII exhibited a low percentage of pathology in the DTA (15%) compared to male (XYM) mice (44%). Moreover, surprisingly, XX gonadal male (XXM) mice infused with AngII also exhibited a low percentage of DTA pathology (8%), similar to XXF mice. In contrast, XY gonadal female (XYF) mice had robust DTA pathology (50%) to a similar level as XYM, even though the level of circulating testosterone was reported to be 7-fold lower in XYF than XYM mice[10, 12].

Figure 2B:
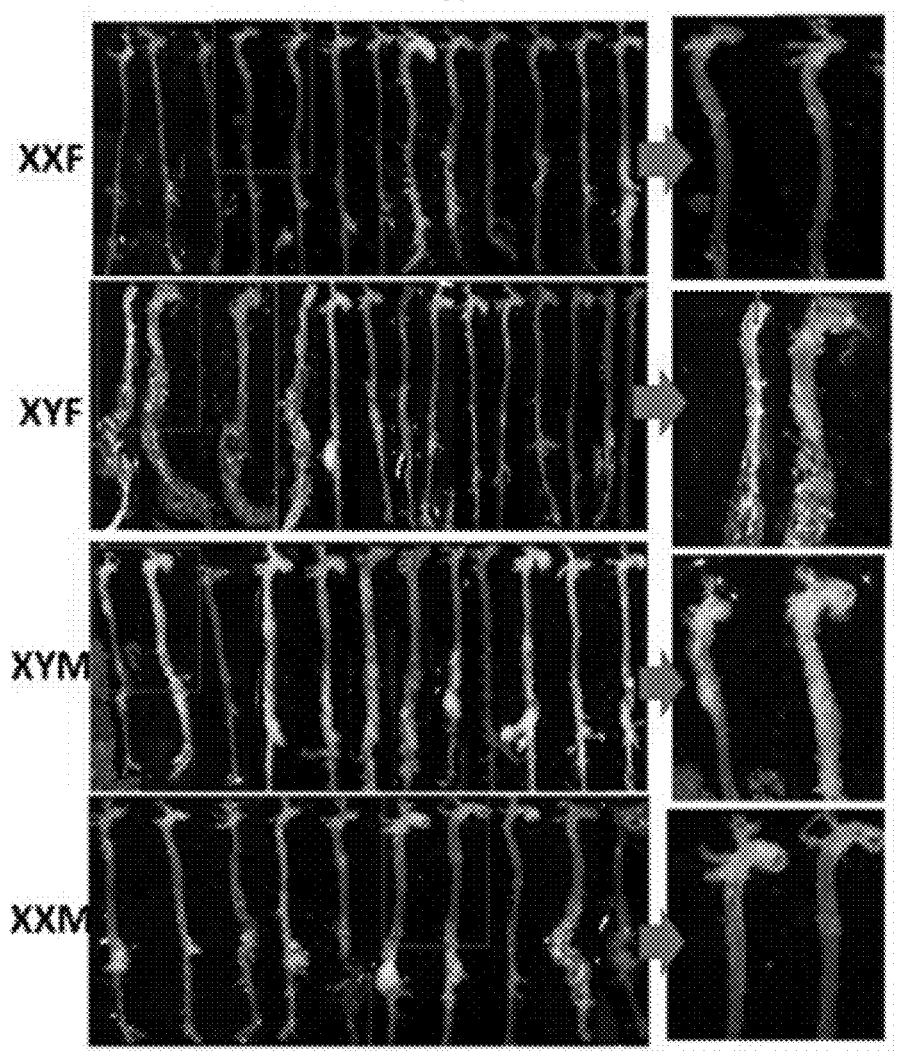

FIG. 2B includes pictures of cleaned, excised aortas at study endpoint in mice of each sex chromosome complement, to illustrate the extent of pathology. Moreover, an enlarged image of the DTA region from two aortas from each group is illustrated in the panels in the right portion of FIG. 2B. In general, XXF and XXM mice had translucent DTA, while XYF and XYM had opaque enlarged aortas indicative of pathology.

Figure 3:
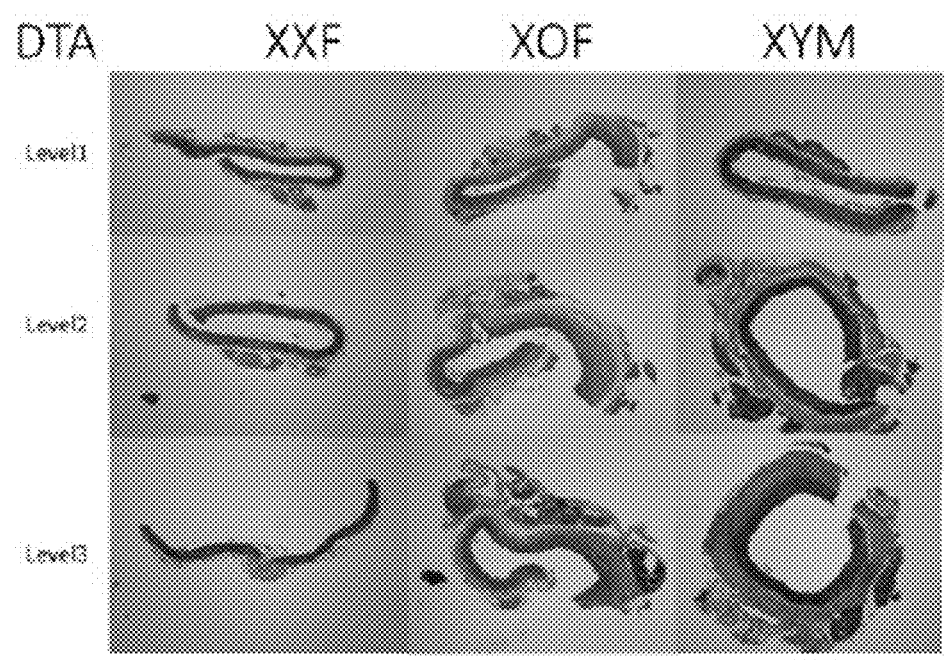
FIG. 3. DTA tissue sections from mice of each genotype. Three levels throughout the DTA are illustrated from n=1/genotype. Sections are stained with Van Gieson.

Paraffin embedded aortas from mice of each sex chromosome complement genotype were serially sectioned. Sections at three different levels along the DTA were stained with Van Geisen to illustrate collagen and elastin. DTA sections from XYM mice infused with AngII exhibited pronounced adventitial expansion compared to sections from XXF, with little evidence of differences in the aortic media between genotypes (FIG. 3). These results demonstrate that AngII causes the formation of aortic pathology in the DTA of XY mice, regardless of gonadal sex. In contrast, XX mice exhibited resistance to AngII-induced DTA pathology, despite the presence of testosterone.

Figure 4A:
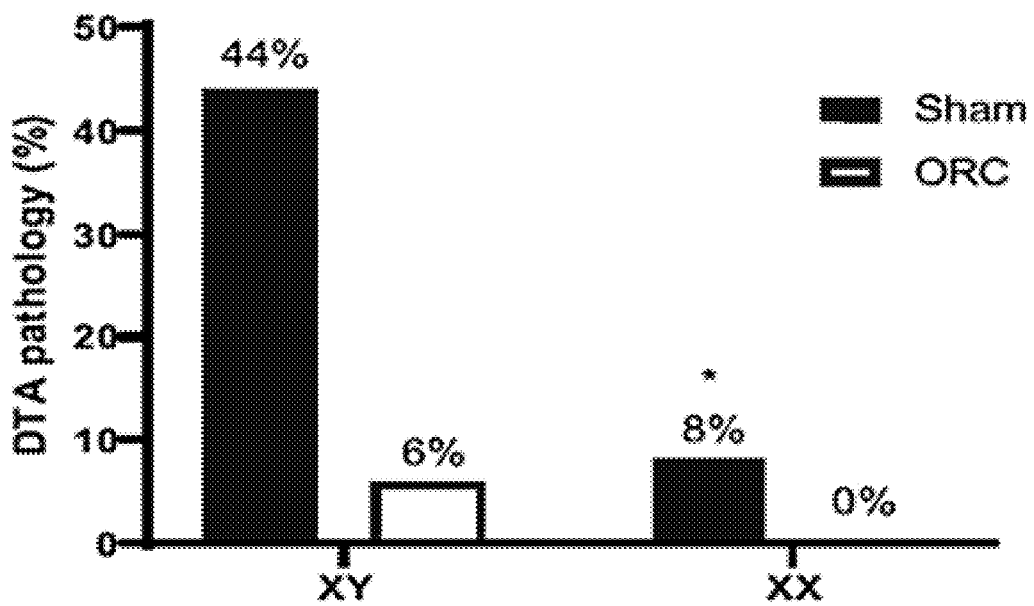
FIG. 4A. The percentage of DTA pathology of AngII-infused sham-operated and orchiectomized (ORC) XYM and XXM mice.
Figure 4B:
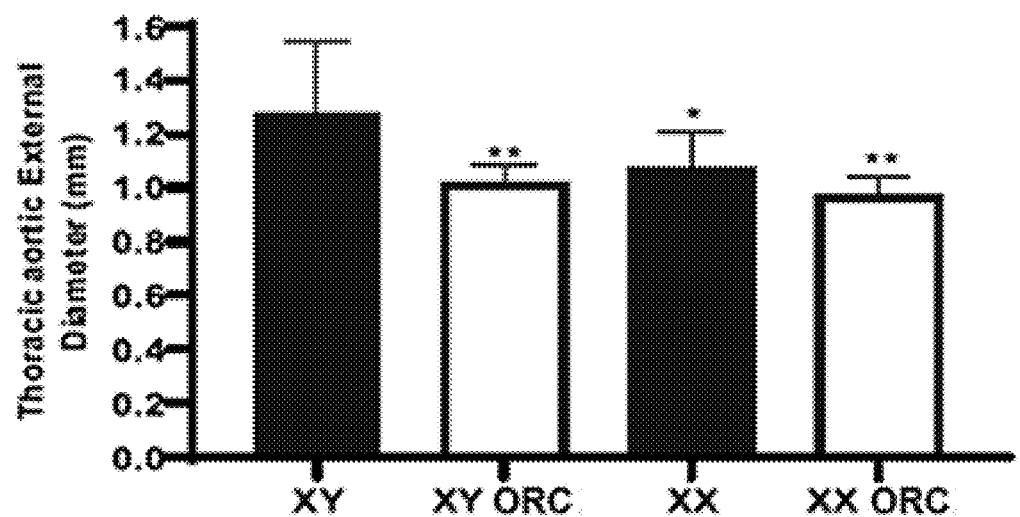
FIG. 4B. Maximal external diameters of DTA. Data are mean±SEM from n=10-15/group. *, $P<0.05$ compared to XYM within group. **, $P<0.05$ compared to sham within genotype.

It was demonstrated that testosterone promotes AngII-induced aortic pathology in both male and female mice.[11-13] Thus, XYM and XXM mice that were castrated two weeks prior to AngII infusion were included. Results demonstrate that orchiectomy (ORC) of XYM and XXM mice resulted in a significant reduction in the percentage of mice exhibiting DTA pathology from AngII infusion (FIG. 4A), as well as a reduction in the maximum external diameter of thoracic aortas from mice of each genotype (FIG. 4B).

These results demonstrate that testosterone is a stimulus for heightened AngII-induced pathology in the DTA of male mice, with more pronounced effects of testosterone to promote AngII-induced DTA pathology in XY than XX males.

Example 2: Abdominal Aorta (AA) Pathology

Figure 5A:
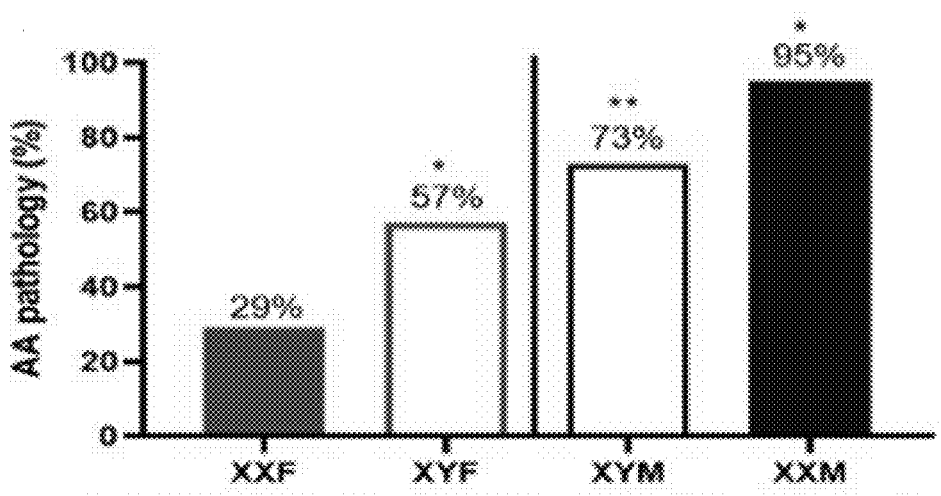
FIGS. 5A and 5B. AngII-induced AA pathology in Four Core Genotype XXF, XYF, XYM and XXM mice.

Previous studies demonstrated that XYM mice exhibit 4-10 fold higher incidence of pathology in the suprarenal aorta in response to AngII infusion than XXF.[10] The FCG model was used on an Ldlr$^{-/-}$ background to define the role of sex chromosome complement genotype on AngII-induced AA pathology. Similar to previous findings, XXF mice were resistant to induction of AA pathology following AngII infusion (29% incidence, FIG. 5A) compared to XYM (73%). However, XYF mice exhibited a high percentage (57%) of AA pathology when infused with AngII to a level that was not statistically significant from XYM.

Figure 5B:
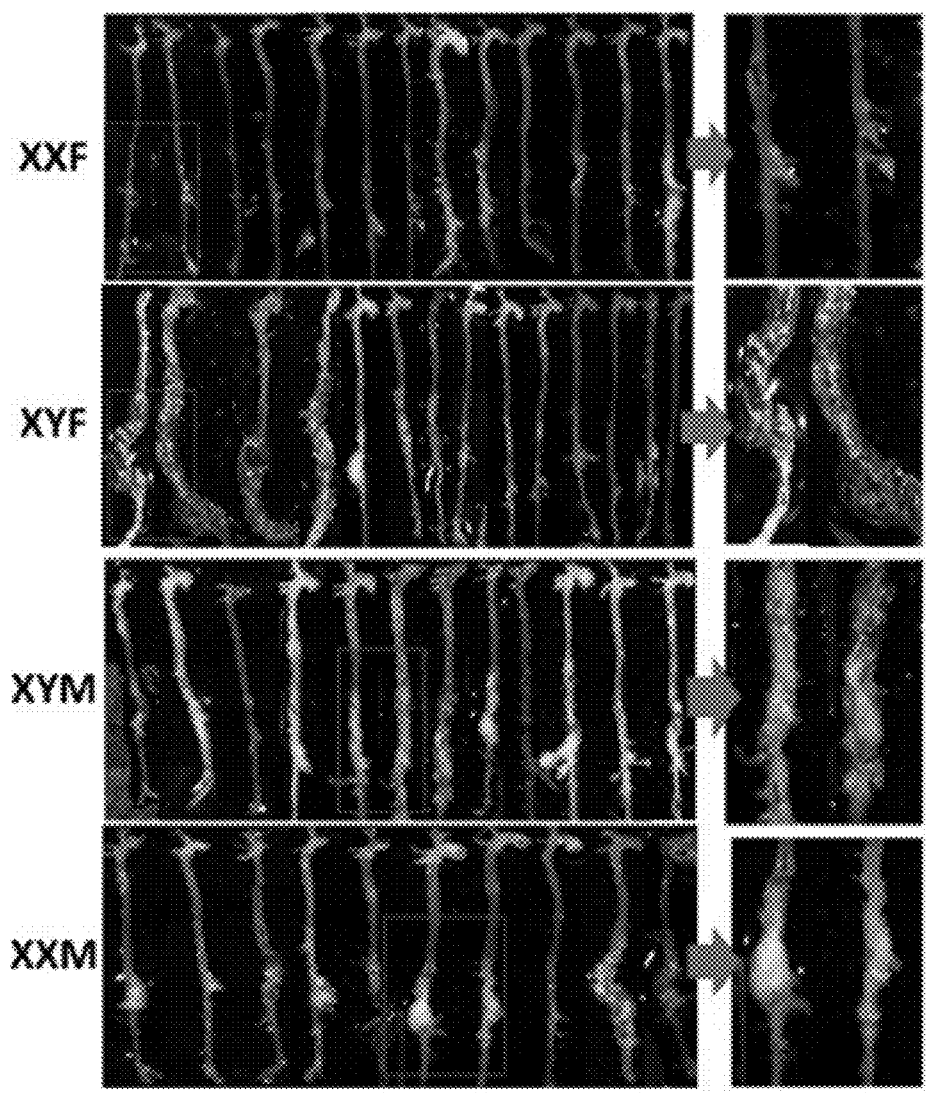
Figure 6:
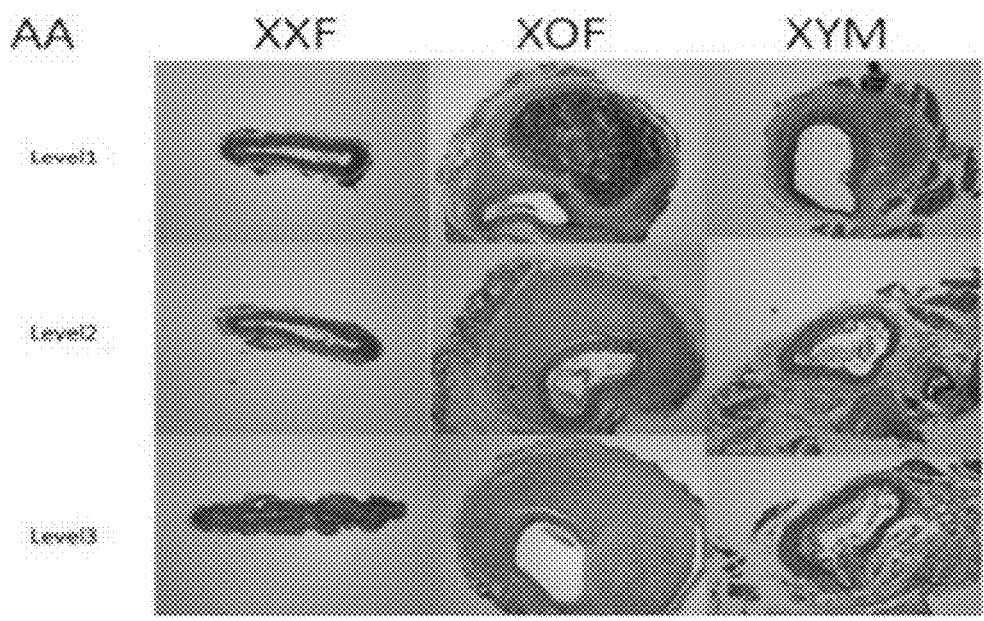
FIG. 6. AA tissue sections from XXF, XOF, and XYM mice. Three levels throughout the AA are illustrated from n=1/genotype. Sections are stained with Van Gieson.

Surprisingly, rather than exhibit a reduction in AA pathology, XXM mice exhibited a higher percentage (95%) of pathology in the AA compared to XYM. Aortas from mice of each genotype are illustrated (FIG. 5B) with an enlargement of the AA region from two representative mice/group. The severity of AA pathology was pronounced in XYF and XYM. Interestingly, XXM mice exhibited focused bulbous pathology restricted to the AA region in response to AngII (FIG. 5B). In AA tissue sections from XYM mice there was adventitial expansion at all three levels, which was not evident in XXF mice (FIG. 6). These results demonstrate that AngII induces aortic pathology in the AA of XY mice, regardless of gonadal sex. Moreover, surprisingly, AngII-induced AA pathology is restricted to the AA region of XXM mice.

Figure 7A:
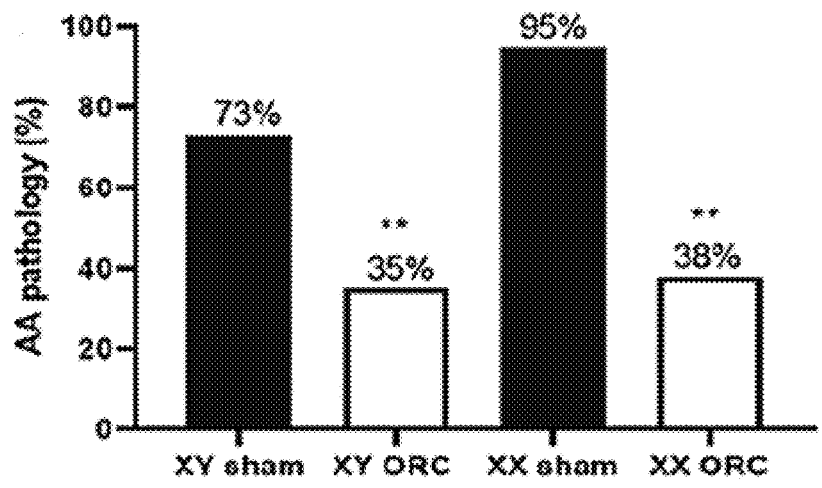
FIG. 7A. Percentage of AA pathology of AngII-infused sham-operated and ORC XYM and XXM mice.
Figure 7B:
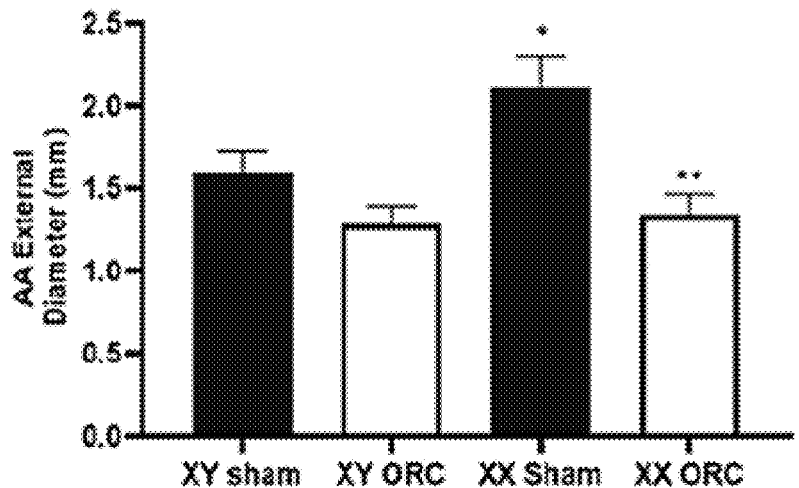
FIG. 7B. Maximal external diameters of AA. Data are mean±SEM from n=10-15/group. *, $P<0.05$ compared to XYM within group. **, $P<0.05$ compared to sham within genotype.

Removal of male sex organs markedly reduced the percentage of AA pathology in both XYM and XXM AngII-infused mice (FIG. 7A). Surprisingly, maximal external diameters of the AA were significantly larger in XXM than XYM, and pathology was reduced by ORC (FIG. 7B). Potentially, this could be due to the concentration of disease to this aortic region of XXM, with minimal pathology in other aortic regions.

These results demonstrate that testosterone is a stimulus for severe AngII-induced AA pathology. Moreover, an intriguing finding from these studies is that placement of an XX aorta within a male with testosterone resulted in focal pathology within the AA region in response to AngII, which is in contrast to the diffuse pathology exhibited in AngII-infused XYM mice.

An important question is whether the ability of AngII to induce sexually dimorphic aortic pathology arises from the presence of two X chromosomes in females, or from the presence of the Y chromosome (plus testosterone) in males. A female $Ldlr^{-/-}$ mice was created with one X chromosome (XOF) using XY* male mice with an aberrant pseudoautosomal region (PAR) that recombines variably with the X PAR during meiosis[135]. For these studies, XXF and XOF were compared to XYM mice infused with AngII. The percentage mice with pathology in the DTA or AA in each genotype were quantified. In addition, aortic weights (normalized to body weight) were quantified as an additional measure of the diffuse nature of AngII-induced aortic pathology.

Figure 8A:
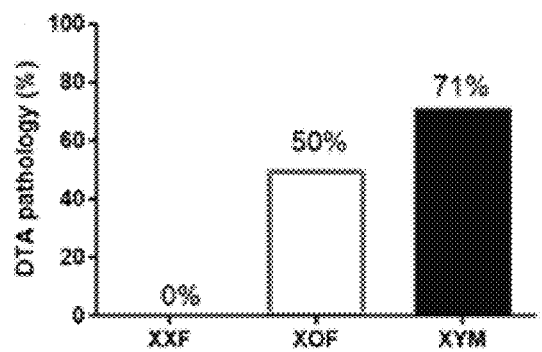
FIG. 8A-8D. AngII-induced DTA and AA aortic pathology in XXF, XOF, and XYM mice. Percentage of DTA (FIG. 8A) and AA (FIG. 8B) pathology. Aortic tissue weights (FIG. 8C). Aortas from mice of each group (FIG. 8D). Data are mean±SEM from n=10-15/group.
Figure 8B:
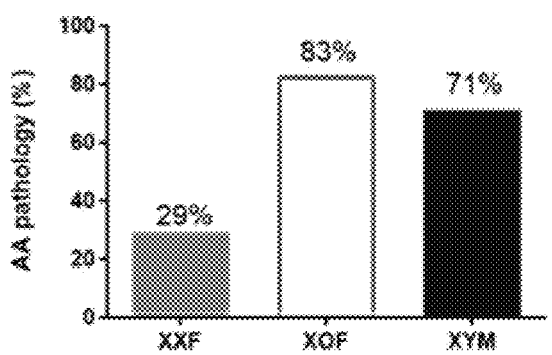
Figure 8C:
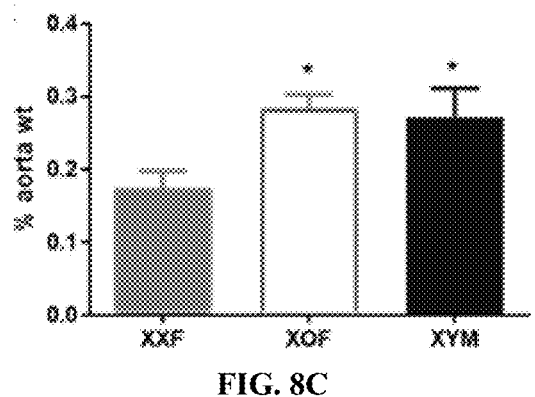
Figure 8D:
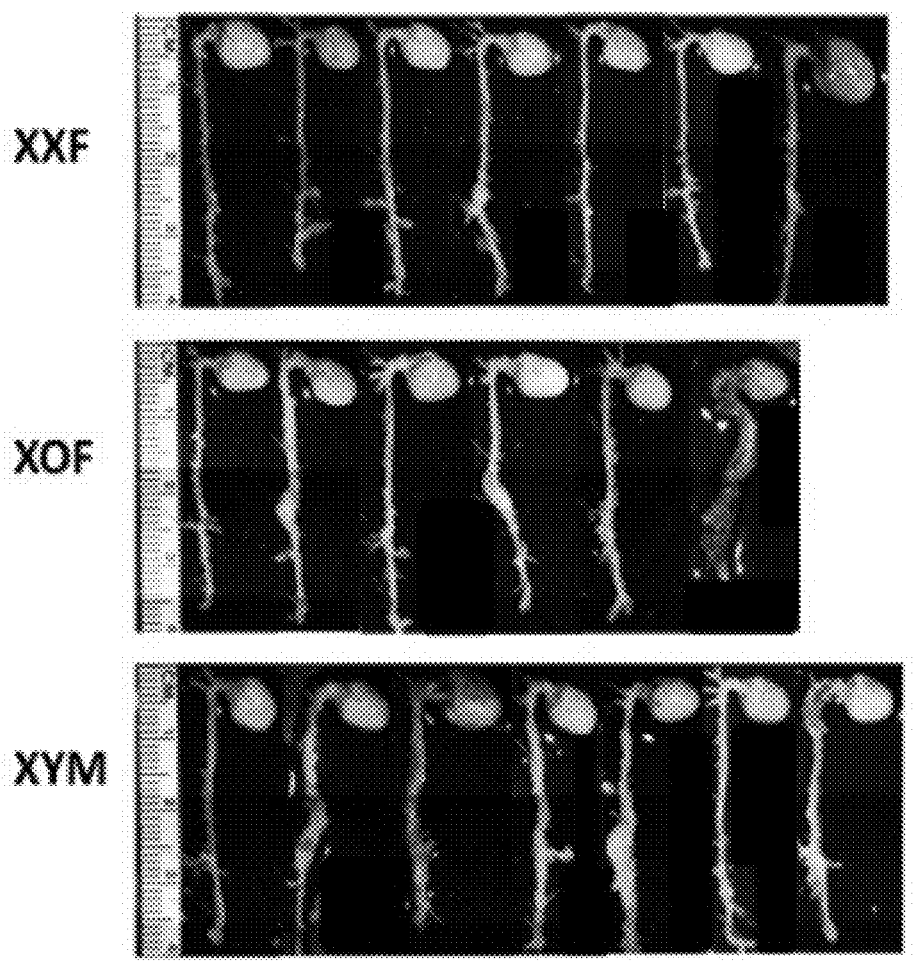

As reported previously[10], pathology of the DTA or AA was minimal in AngII-infused XXF mice (FIGS. 8A, 8B). In contrast, XOF mice exhibited similar high percentages of aortic pathology in the DTA and AA as XYM mice infused with AngII (FIGS. 8A, 8B). Moreover, aortic weights were similar between AngII-infused XOF and XYM (FIG. 8C), and aortic pathology was severe (FIG. 8D). Analysis of tissue morphology illustrates adventitial expansion in the DTA of XOF mice in response to AngII, which was even more pronounced in the AA of XOF mice (FIG. 3 and FIG. 6). These results demonstrate that two X chromosomes protect female mice from AngII-induced aortic pathology in a region-specific manner. See also, FIG. 1 (depicting AngII invoking s a 5HT3R mechanism to promote sexually dimorphic aortic pathology in a region-specific manner, with effects augmented by nicotine, a well-known risk factor and initiator of aortic pathology).

Example 3: Differentially Expressed Genes (DEGs)

Figure 9A:
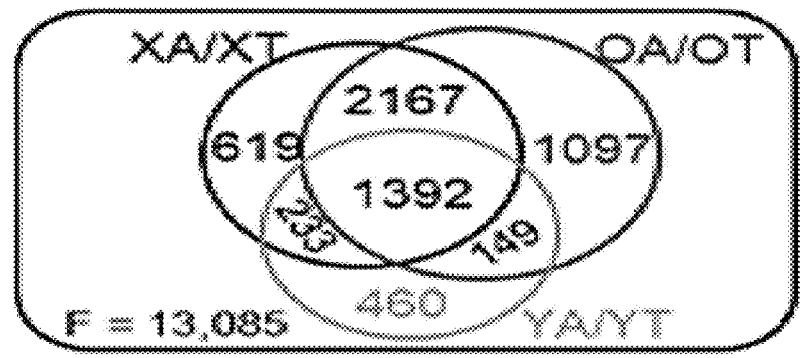
FIG. 9A. Venn diagram of DEGs ($q<0.01$) for abdominal (A) vs thoracic (T) transcriptional profiles. F=total genes.

To begin to elucidate mechanisms for the region-specific effects of AngII to induce aortic pathology, RNAseq was performed on DTA and AA from XXF, XOF and XYF $Ldlr^{-/-}$ mice (mice were not infused with AngII, but were fed a Western diet for 1 week). Multiple testing identified significant (q≤0.01) regional effects (FIG. 9A). 1,392 genes were differentially expressed (DEGs) between abdominal and thoracic aortic regions across all three genotypes.

Figure 9B:
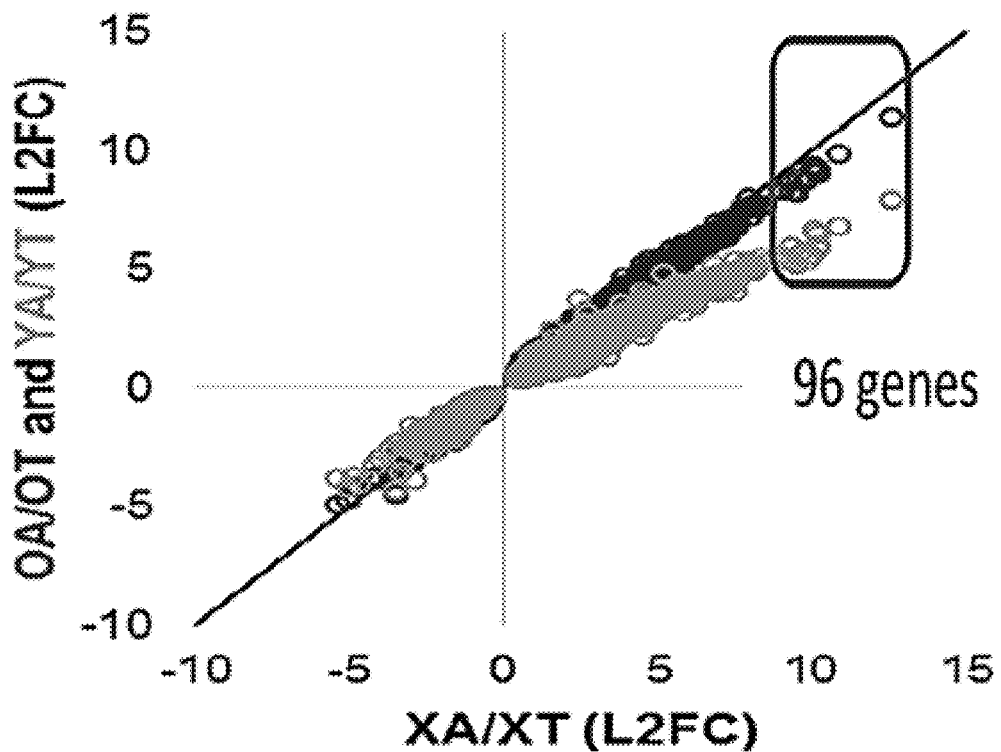
FIG. 9B. 1,392 DEGs across all genotypes plotted as log 2-fold changes (L2FC) between A and T of XXF (black line as 1:1 reference), XYF (gold) and XOF (red).

Log 2-fold changes (L2FC) of DEGs were plotted between aortic regions from XXF (black line plotted as reference for 1:1 effect) versus XOF (dark gray) and XYF mice (light gray; FIG. 9B). Genotype XY showed less intense DEGs between aortic regions, most especially for genes that were upregulated in abdominal aorta (96 genes that fell off of the line correlation). Gene Ontology functional analysis demonstrated strong overrepresentation for neuronal signatures (29 genes). Using this approach, the top-ranked neuronal genes were Htr3a and Htr3b. Further, the expression levels of these two genes were strongly correlated with one another (r=0.988) across subjects, supporting that they participate as subunits of 5HT3R pentamers.

Figure 10:
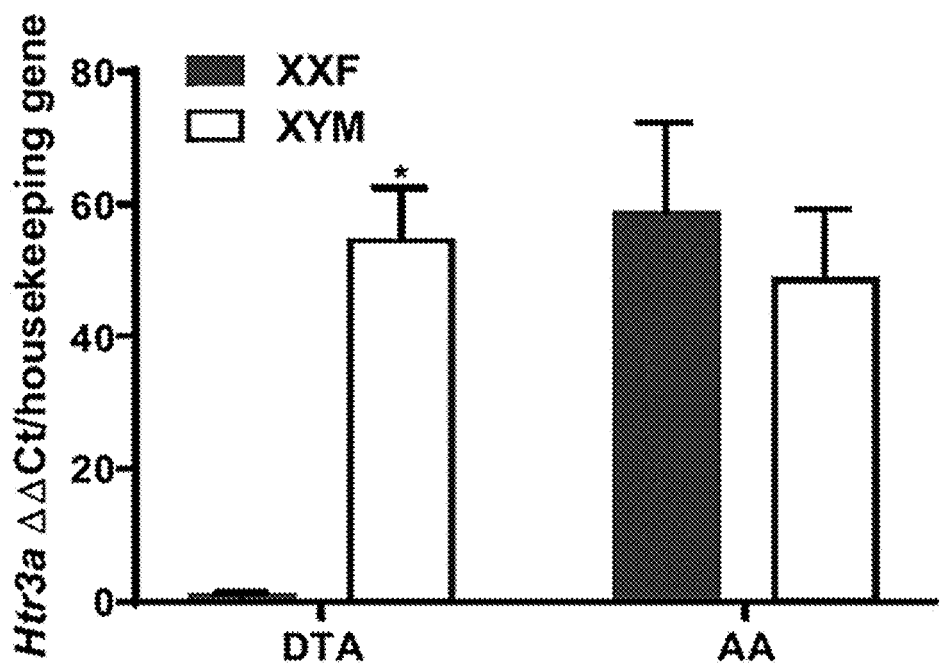
FIG. 10. Htr3a mRNA abundance in DTA and AA of XXF and XYM mice. Data are mean±SEM from n=5 mice/group. *, $P<0.05$ compared to XXF within region.

Attention was given to mRNA abundance of Htr3a, the required functional A subunit, which exhibited more uniform expression levels between DTA and AA of XYF and XOF. In XYM, Htr3a mRNA abundance was equivalent between aortic regions (FIG. 10). However, aortas of XXF exhibited pronounced regional differences in Htr3a mRNA abundance, with 54-fold lower expression levels in DTA than AA. These results indicate that (1) Htr3a expression levels are uniform along the aorta of XY mice, (2) in contrast, DTA of XX mice express much lower levels of Htr3a than AA. The robust regional difference in Htr3a mRNA abundance between DTA and AA of XX, but not XY mice is hypothesized to contribute to region-specific effects of AngII to induce aortic pathology.

Example 4: Release of 5HT to Activate 5HT3R and Promote Aortic Pathology

Figure 11:
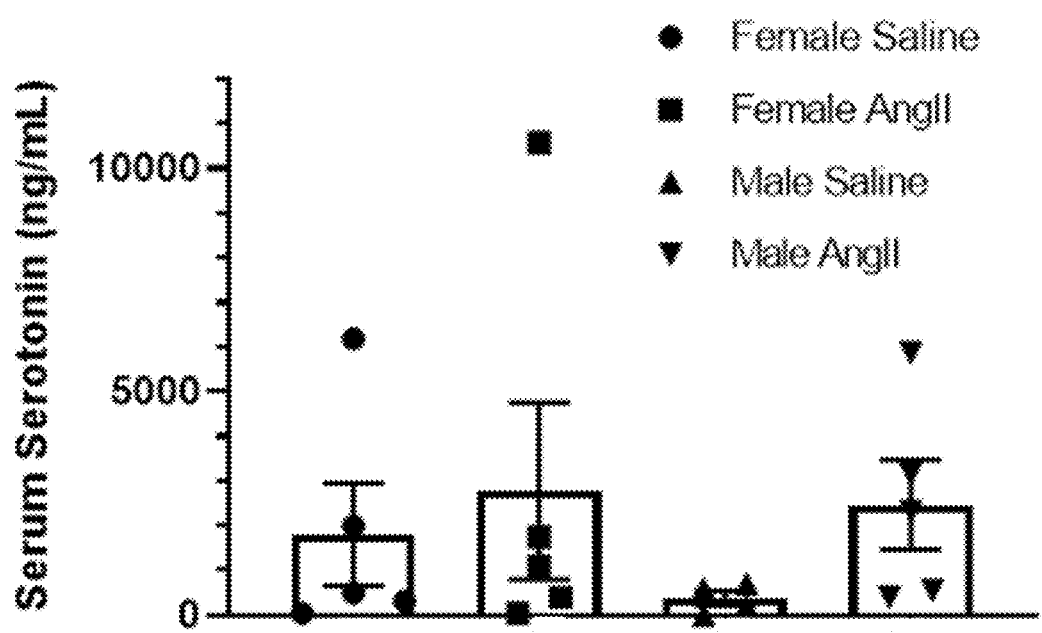
FIG. 11. Infusion of AngII (for 5 days) results in modest increases in serum 5HT (serotonin) concentrations of male mice. Data are mean±SEM with dots representing individual mice.

AngII has been reported to stimulate the release of 5HT from central neurons.[72-76] The ability of Trop to markedly reduce AngII-induced aortic pathology implies interactions between the RAS (e.g., AngII) and the serotonergic system. Serum 5HT concentrations were quantified in XYM and XXF $Ldlr^{-/-}$ mice infused with saline or AngII for 5 days. Preliminary results indicate that infusion of AngII for a short duration results in modest elevations of serum 5HT concentrations of XYM mice, with a trend toward increases in females (FIG. 11). These results indicate that AngII invokes release of 5HT to activate 5HT3R and promote aortic pathology.

Example 5: Nicotine Augments AngII-Induced Aortic Pathology

Figure 12A:
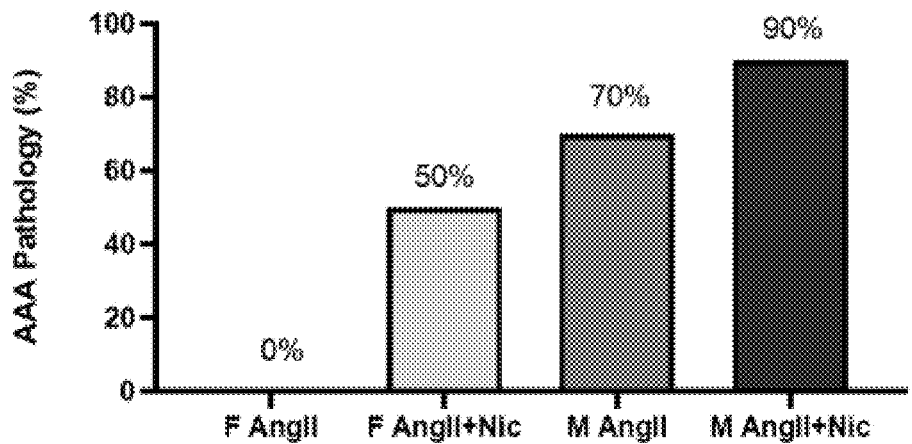
FIG. 12A-12C. Co-infusion of nicotine with AngII promotes aortic pathology.
Figure 12B:
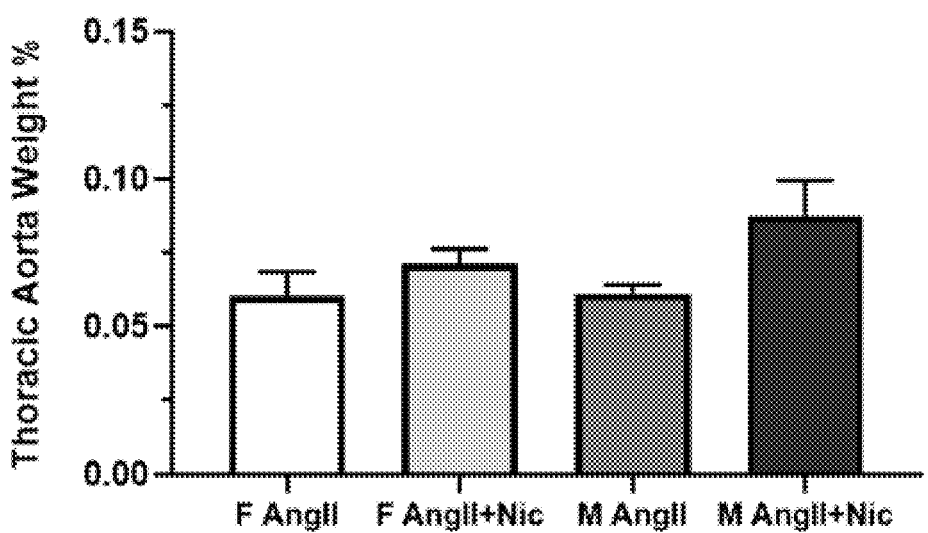
Figure 12C:
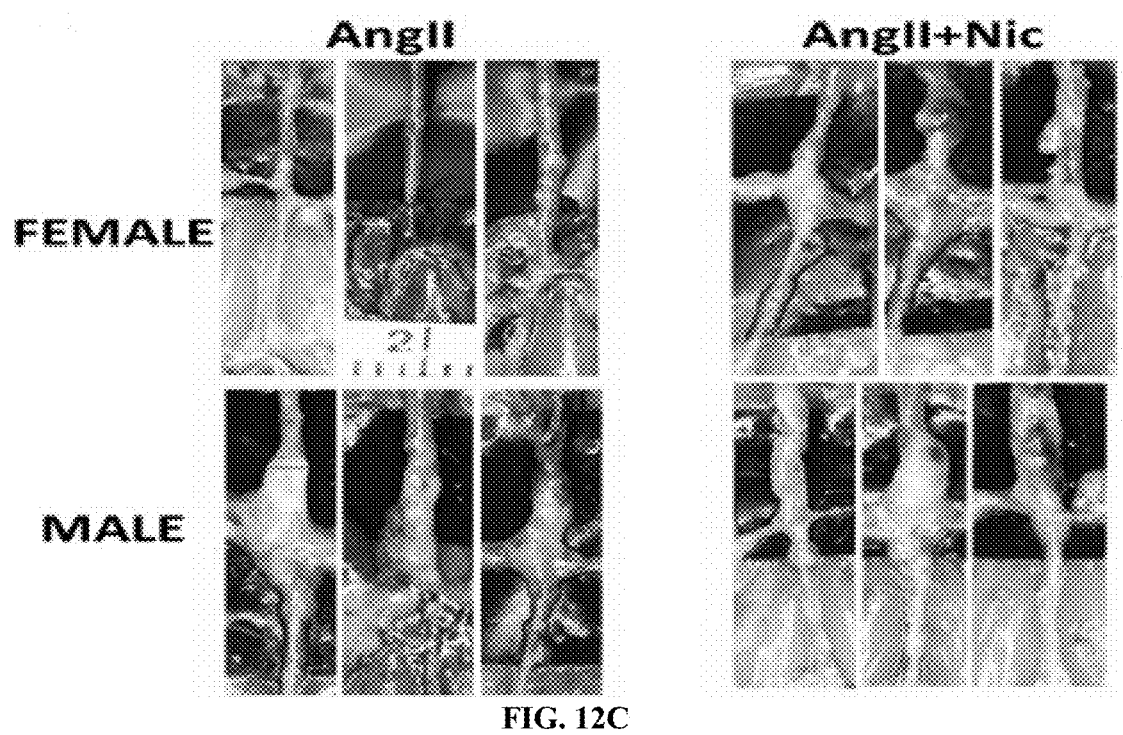

5HT3R shares 30% homology with nicotinic receptors[18, 137], and nicotine has been demonstrated to promote aortic pathology.[121, 128-130] Thus, the effects of nicotine on regional aortic pathology induced by AngII were investigated in XXF and XYM $Ldlr^{-/-}$ mice. Mice were fed a Western diet beginning one week prior to co-infusion of AngII (1,000 ng/kg/min) and nicotine (4 mg/kg/day[130]). Ultrasound as used to quantify internal lumen diameters of AA to calculate the percentage of mice with pathology (50% increase compared to day 0 of infusions; FIG. 12A). Remarkably, co-infusion of nicotine with AngII resulted in pathology within the AA in 50% of XXF mice (FIG. 12A). Moreover, the percentage of XYM with AA pathology increased with co-infusion of nicotine (FIG. 12A). Aortas were harvested for RNA extraction, and thus DTA maximal diameters could not be quantified at study endpoint. However, the weight of the thoracic aorta was increased in both sexes, with significant increases observed in XYM mice co-infused with nicotine and AngII (FIG. 12B). Moreover, in representative in situ illustrations, the ability of nicotine to cause focal AA pathology in AngII-infused XXF, while causing more severe aortic pathology of XYM was evident (FIG. 12C).

Figure 13:
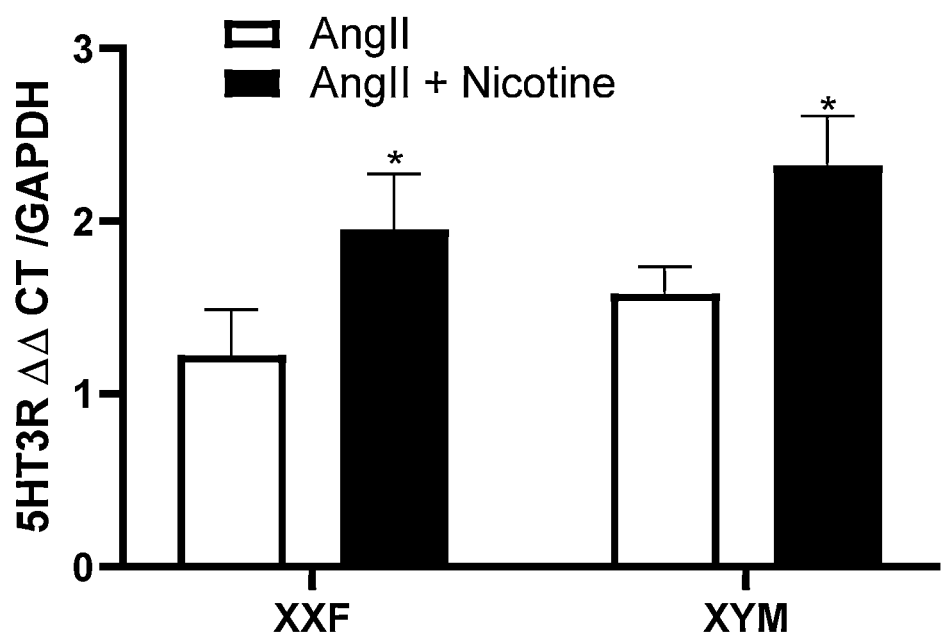
FIG. 13. Htr3a mRNA abundance in AA of mice infused with AngII in the absence of presence of nicotine. Data are mean±SEM from n=5 mice/group. *, $P<0.05$ compared to AngII.

To define potential mechanisms for these effects, and whether they are linked to 5HT3R, Htr3a mRNA abundance was quantified in DTA and AA of XXF and XYM AngII-infused mice. Nicotine had no effect on Htr3a mRNA abundance in DTA (data not shown). However, in AA, co-infusion of nicotine with AngII resulted in a significant increase in Htr3a mRNA abundance in XXF and XYM mice (FIG. 13).

These results demonstrate that nicotine augments AngII-induced aortic pathology in both sexes, with potentially more focal nicotine augmentation of AA pathology in XXF, and more diffuse potentiation of both DTA and AA pathology in XYM. Moreover, nicotine increased Htr3a mRNA abundance in a region-specific manner of both XXF and XYM mice.

Example 6: Aortic Htr3a Abundance

Figure 14:
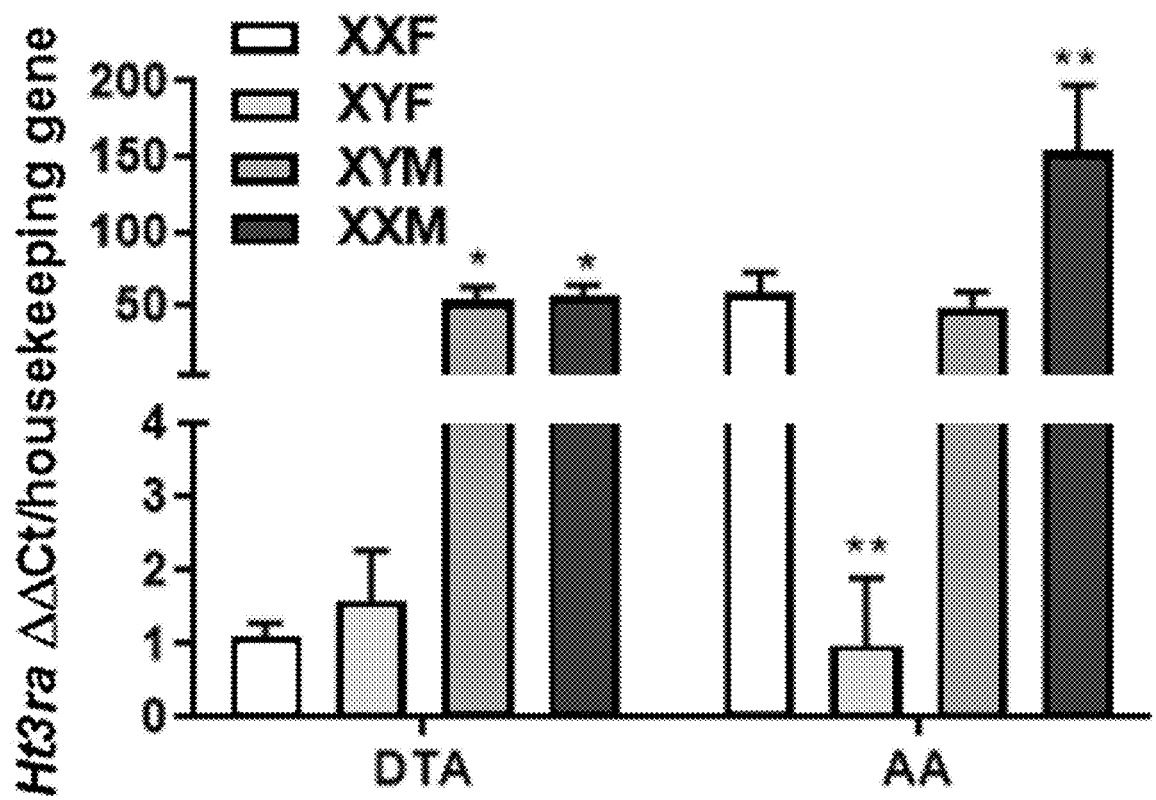
FIG. 14. Htr3a mRNA abundance in DTA vs AA of XX and XYF, and XY and XXM. Data are mean±SEM from n=5 mice/group. *, $P<0.05$ compared to AngII.

Htr3a mRNA abundance differs between DTA and AA of male and female mice (FIG. 10). In studies to determine if sex hormones or sex chromosomes impact this regional Htr3a expression the FCG model was used. In DTA, Htr3a mRNA abundance was markedly higher in both XYM and XXM compared to XXF and XYF, indicating a robust effect of sex hormones to promote DTA Htr3a mRNA abundance (FIG. 14). In contrast, Htr3a mRNA abundance in AA tracked the number of X chromosomes, with higher Htr3a mRNA abundance in female and male XX than XY mice of either sex, indicating an effect of sex chromosome genotype. Moreover, while there were no differences in Htr3a mRNA abundance between AA of XXF and XYM mice, higher expression levels were observed in XYM than XYF mice, and in XXM than XXF mice, supporting both sex hormone and sex chromosome-dependent regulation.

Figure 15:
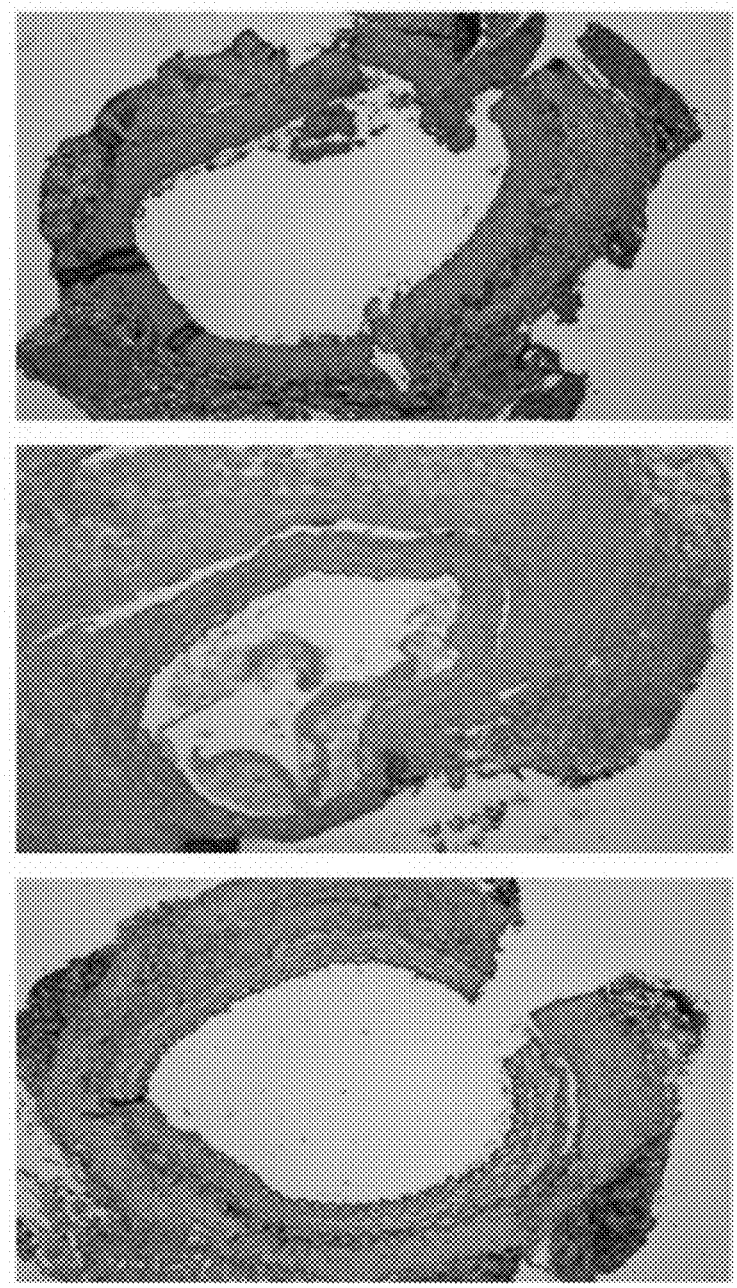
FIG. 15. 5HT3R immunohistochemistry of DTA and AA tissue sections from AngII-infused mice. Top, DTA from XYM; middle, AA from XOF; bottom, DTA from XYM mice with secondary (2°) antibody only.

Immunohistochemistry was performed for 5HT3R using paraffin embedded tissue sections of DTA and AA from AngII-infused XYM and XOF mice. DTA or AA tissue sections from each sex chromosome complement genotype were incubated with a polyclonal 5HT3aR antibody (NB100-56351, Novus Biologicals; 5 μg/ml). Control sections were incubated with secondary antibody only (goat anti-rabbit IgG, ImmPRESS, MP7451, Novus Biologicals). Results demonstrate positive 5HT3aR immunostaining in the media and adventitia from DTA and AA sections from AngII-infused XYM or XOF mice (FIG. 15).

Example 7: 5HT3R-Mediated Mechanisms in Aortic Smooth Muscle Cells

Figure 16:
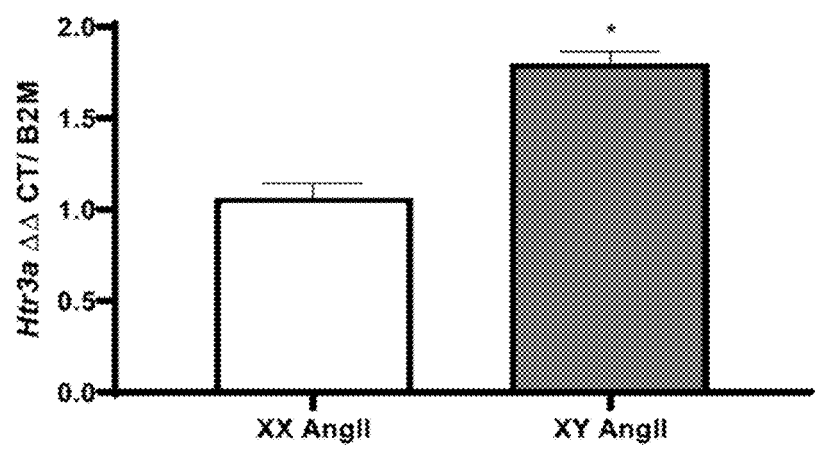
FIG. 16. Htr3a mRNA abundance in aortic smooth muscle cells (ASMC) incubated with AngII. Data are mean±SEM from n=4 batches of cells from each genotype. *, $P<0.05$ compared to XX AngII.

Smooth muscle cells are known to express 5HT3R[87], but the role of this receptor subtype in aortic smooth muscle cells (ASMC) function and disease development is unknown. Data demonstrate that (1) DTA and AA tissue sections from AngII-infused XYM or XOF mice exhibit positive 5HT3aR immunoreactivity in aortic media (FIGS. 3, 6); (2) ASMCs isolated from AA of XXF and XYF mice express Htr3a mRNA, and that in cells treated with AngII (1 μM), Htr3a mRNA abundance is higher in ASMCs from XY than XX females (FIG. 16). Finally, short-term infusion of AngII modestly increased serum 5HT concentrations of XXF and XYM mice (FIG. 11), suggesting that AngII may increase ligand concentrations to act at 5HT3R in relevant cell types that participate in the development of aortic pathology. AngII acts at AT1R, a G-protein coupled receptor, to elicit a variety of signaling cascades that influence aortic pathology. 5HT actions at 5HT3R open ion channels on excitable cells, such as ASMC, that increase channel permeability to $Na^+$ and $K+^{15, 84}$. In addition, 5HT3R exhibit both direct sensitivity to influx calcium through the channel pore[87, 139] as well as $Na^+/K^+$-mediated depolarization-induced increases in intracellular calcium. There are no known reports on interactions between AT1R and 5HT3R in any cell type.

Example 8: 5HT3R Antagonist Decreased DTA and AA Pathology in a Dose Dependent Manner Tropisetron (Trop) is an exemplary 5HT3R antagonist used in these studies.[136] Effects of Trop were tested against AngII-induced aortic pathology in XY male Ldlr−/− mice (XYM). XYMs were selected for studies as this sex chromosome complement genotype exhibits pathology from AngII infusion in DTA and AA. Mice were fed a Western diet (high fat, high sucrose, high cholesterol) beginning one week prior to the start of treatments. XYM Ldlr−/− mice were administered two different doses of Trop (10 or 20 mg/kg/day) by osmotic minipump for 7 days. The minipumps were then replaced with new pumps containing both AngII (1,000 ng/kg/min) and Trop and treatment was continued for 28 days. Aortas were removed from the iliac bifurcation to the end of the arch and fixed in formalin. Aortas were then cleaned and weighed.

Figure 17A:
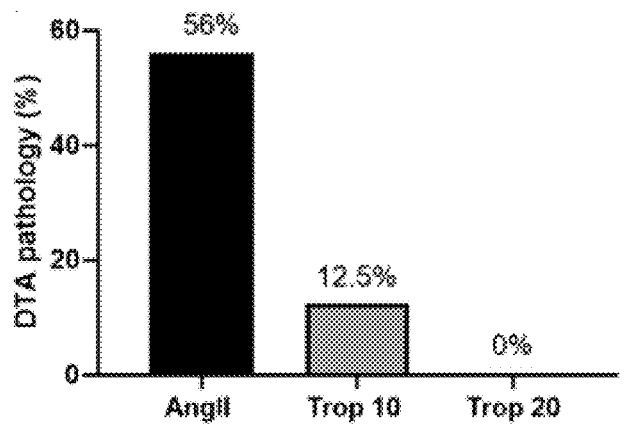
FIG. 17A-17D. Tropisetron (Trop) dose-dependently reduces AngII-induced pathology in the DTA and AA. Percent of XYM mice having pathology in the DTA (A) and AA (B). Aorta weights (C). Aortas from mice of each group (D). Data are mean±SEM from n=15-20 mice/group. *, P<0.05 compared to AngII.
Figure 17B:
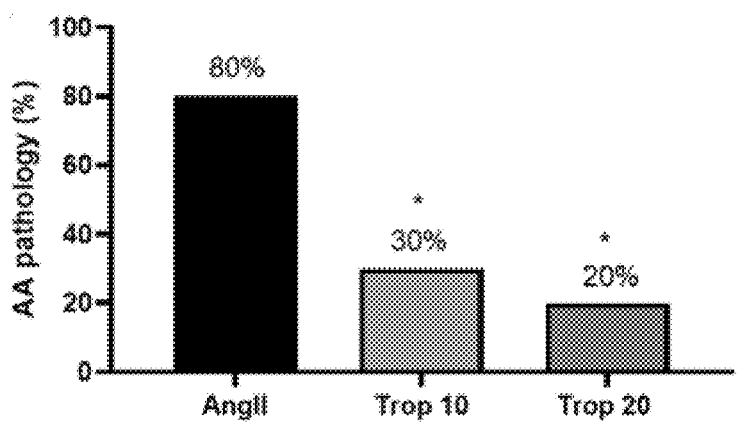
Figure 17C:
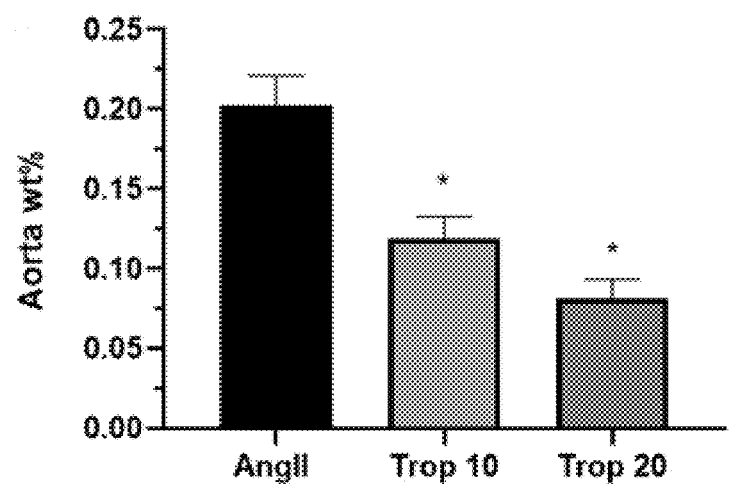
Figure 17D:
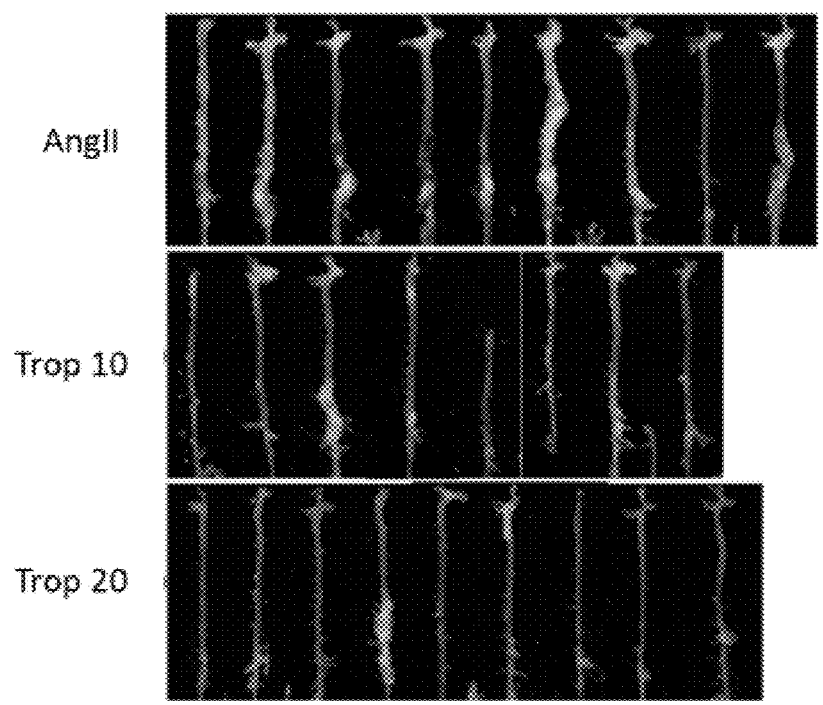

Administration of Trop resulted in a dose-dependent reduction in the percentage of AngII-induced pathology of DTA (FIG. 17A), AA (FIG. 17B) and of aortic weights (FIG. 17C). The mean weight of the aortas from the AngII group was significantly heavier than the weights of the aortas from the tropisetron treated mice. The mean weights for the three groups were: AngII=0.054 g±0.005; Trop 10=0.035 g±0.004; Trop 20=0.023 g±0.003 (±SEM). This is an additional indication of greater diffuse disease in the aortas from the AngII group. Moreover, aortas of AngII-infused mice administered Trop were translucent with minimal pathology (FIG. 17D). These results demonstrate that functional blockade of 5HT3R has a striking effect to reduce AngII-induced pathology in the DTA and AA of male XY mice.

Example 9: 5HT3R Antagonist Diminished Amount of Increase in the Internal Lumen Diameters of Abdominal Aortas Male mice (XYM Ldlr−/−) were fed a Western diet (high fat, high sucrose, high cholesterol) beginning one week prior to the start of treatments. XYM Ldlr−/− mice were then administered two different doses of Trop (10 or 20 mg/kg/day) by osmotic minipump for 7 days. The minipumps were then replaced with new pumps containing both AngII (1,000 ng/kg/min) and Trop and treatment was continued for 28 days.

Figure 18:
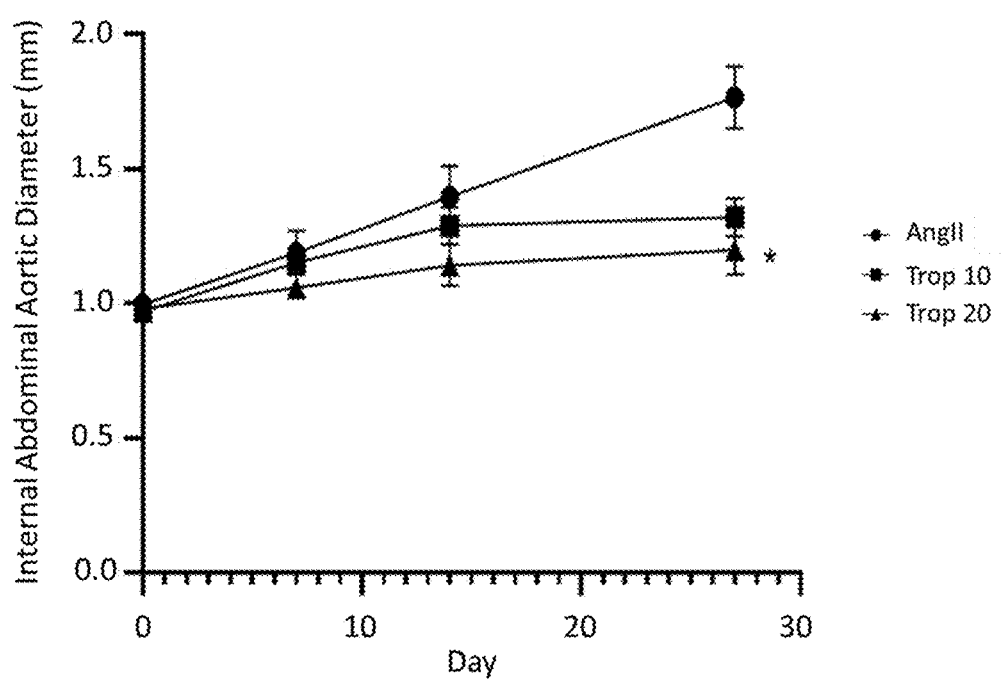
FIG. 18. Internal abdominal aorta diameters measured by ultrasound over time. Trop 20 was significantly different from the AngII group (*P<0.05 compared to AngII).
Figure 19:
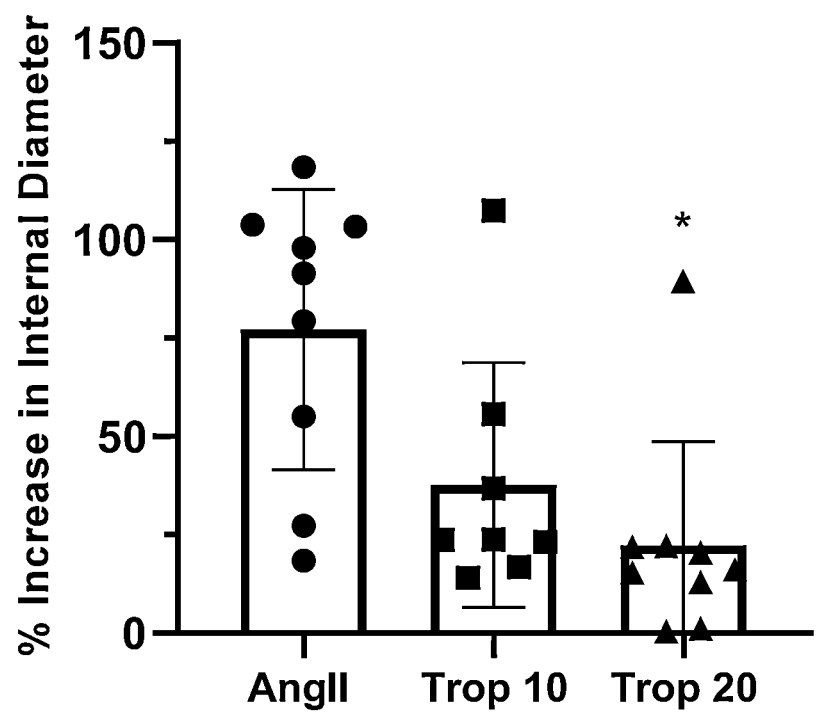
FIG. 19. Percent increase in abdominal aorta diameters on Day 27 compared to Day 0 (baseline). An increase of 50% or more is considered an aneurysm. Trop 20 was significantly different from the AngII group (*P<0.05 compared to AngII).

Ultrasounds of the aortas were used to quantify internal lumen diameters of AA to calculate the percentage of mice with pathology (≥50% increase in internal lumen diameter compared to diameter prior to start of treatments (Day 0)). Internal lumen diameters of abdominal aortas from AngII treated mice treated with either dose of tropisetron were smaller than those from the AngII alone group after 27 days of treatment (FIG. 18). The average diameters on Day 27 were: AngII=1.77±0.35; Trop 10=1.32±0.23; Trop 20=1.20±0.28 (±SEM, *P<0.05 compared to AngII). The average diameters in all three groups increased from their baseline values with the AngII group having the largest increase followed by the Trop 20 and then Trop 10 group. FIG. 19 shows the percent increase in internal lumen diameters from Day 0 (baseline) to Day 27. An increase of 50% or more is considered an aneurysm.

Figure 20:
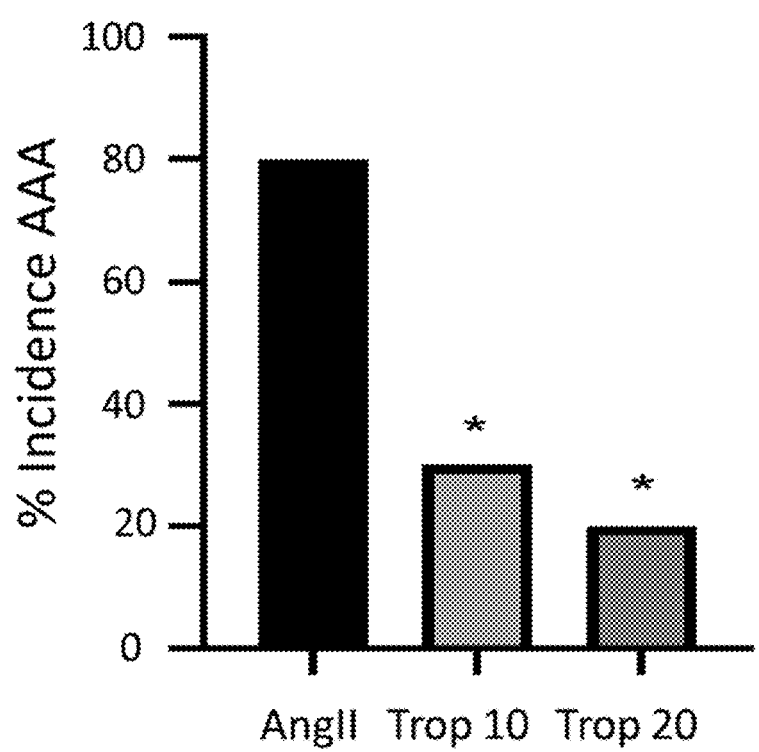
FIG. 20. Incidence of abdominal aortic aneurysms. Mice that died before the end of the study were necropsied and included in the incidence data. * P=<0.05 compared to AngII.

Example 10: Treatment with 5HT3R Antagonist Reduced Incidence and Severity of AngII-Induced Abdominal Aortic Aneurysms Male mice (XYM Ldlr−/−) were fed a Western diet (high fat, high sucrose, high cholesterol) beginning one week prior to the start of treatments. XYM Ldlr−/− mice were then administered two different doses of Trop (10 or 20 mg/kg/day) by osmotic minipump for 7 days. The minipumps were then replaced with new pumps containing both AngII (1,000 ng/kg/min) and Trop and treatment was continued for 28 days. Treatment with tropisetron significantly reduced the incidence and severity of abdominal aortic aneurysms compared to AngII alone (FIG. 20, Table 1).

TABLE 1

Incidence and grading of abdominal aneurysms. Abdominal aneurysms are graded from 0 to 4 according to a scale (see Methods) with 0 = no aneurysm and 4 being a rupture

| Group | % Incidence | Abdominal Aneurysm Grade | | | | |
|---|---|---|---|---|---|---|
| | | 0 | 1 | 2 | 3 | 4 |
| AngII | 80 | 2 | 2 | 1 | 4 | 1 |
| Trop 10 | 30 | 7 | 3 | 0 | 0 | 0 |
| Trop 20 | 20 | 8 | 0 | 1 | 0 | 1 |

Example 11: 5HT3R Antagonist Reduced Systolic and Diastolic Blood Pressure Induced by AngII Male mice (XYM Ldlr−/−) were fed a Western diet (high fat, high sucrose, high cholesterol) beginning one week prior to the start of treatments. XYM Ldlr−/− mice were then administered two different doses of Trop (10 or 20 mg/kg/day) by osmotic minipump for 7 days. The minipumps were then replaced with new pumps containing both AngII (1,000 ng/kg/min) and Trop and treatment was continued for 28 days.

Figure 21A:
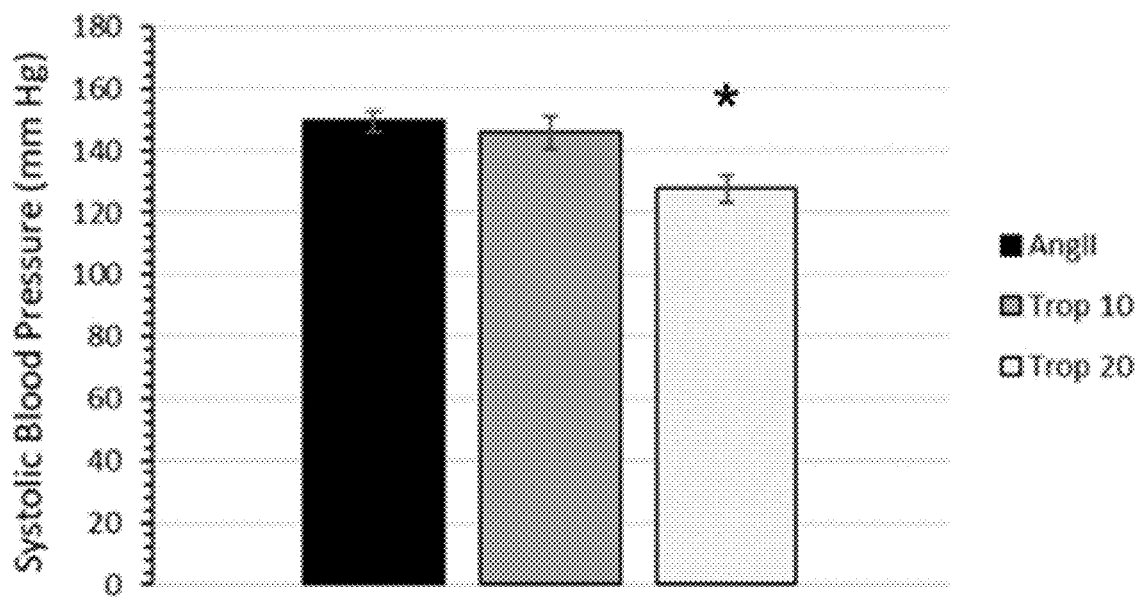
FIGS. 21A and 21B. Blood pressure in mice receiving AngII alone or in combination with either 10 or 20 mg/kg/day Trop.
Figure 21B:
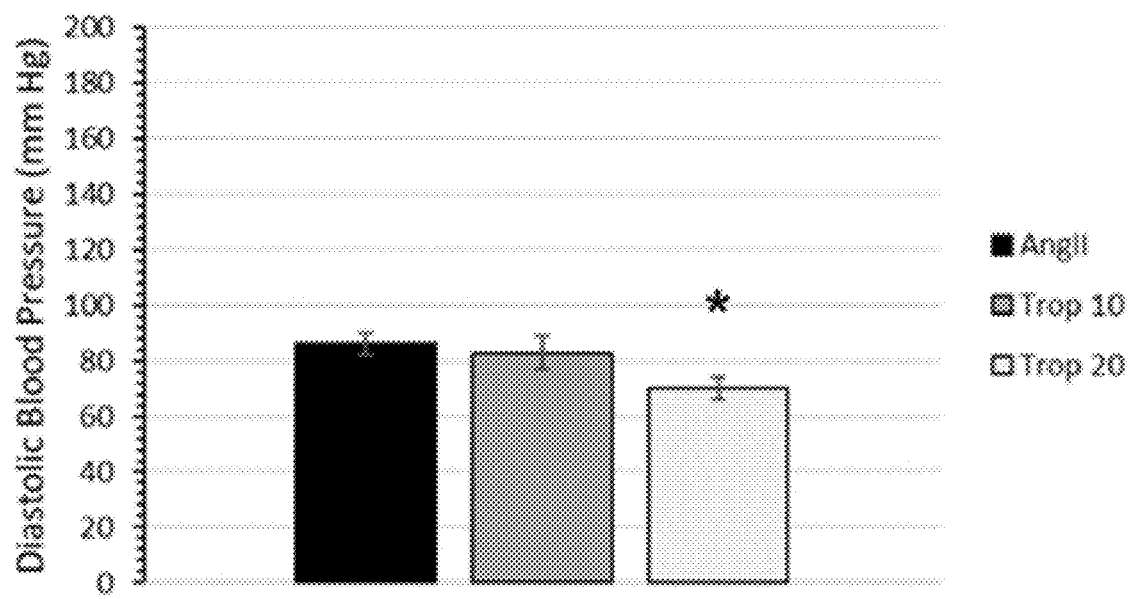

Tropisetron at 20 mg/kg/day significantly reduced both systolic and diastolic blood pressure compared to AngII alone. Blood pressures were taken on five consecutive days. Measurements from the last three days were used to calculate blood pressures for each group. The mean systolic blood pressures are in mm Hg (±SEM): AngII=149±3.4; Trop 10=146±5.6; Trop 20=128±4.4. The mean diastolic blood pressures were in mm Hg: AngII=86±4.0; Trop 10=83±6.0; Trop 20=70±4.1 (FIG. 21).

Example 12: 5HT3R Antagonist Diminished Amount of Increase in External Diameters of Abdominal Aortas Male mice (XYM Ldlr−/−) were fed a Western diet (high fat, high sucrose, high cholesterol) beginning one week prior to the start of treatments. XYM Ldlr−/− mice were then administered two different doses of Trop (10 or 20 mg/kg/day) by osmotic minipump for 7 days. The minipumps were then replaced with new pumps containing both AngII (1,000 ng/kg/min) and Trop and treatment was continued for 28 days. External abdominal aortic diameters were quantified on excised, cleaned tissue mounted on a black wax background. A Nikon SMZ800 dissecting microscope was used to obtain aorta images and the maximal external diameter of the abdominal aorta was measured using Nikon NIS-Elements Version 5.2.

Figure 22:
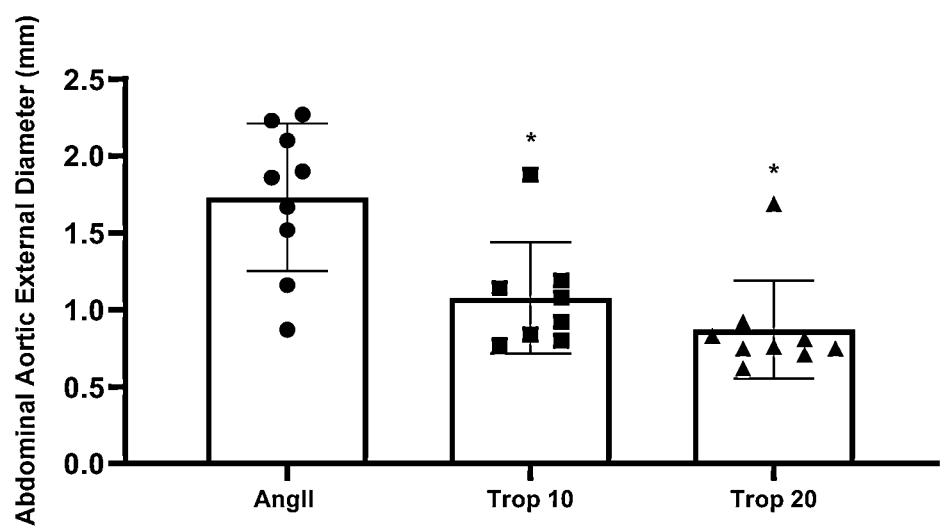
FIG. 22. Abdominal Aortic external diameter measurements. The external diameters of abdominal aortas from both tropisetron groups were significantly smaller than the AngII group (p<0.01).

The external diameters of abdominal aortas from tropisetron treated mice were significantly smaller than from mice treated with AngII alone (p<0.01) (FIG. 22). The mean external diameters (mm±SEM) are: AngII=1.73±0.16, Trop 10=1.08±0.13, and Trop 20=0.87±0.11.

Example 13: 5HT3R Antagonist Treatment Diminished Atherosclerosis in Aortic Arch Male mice (XYM Ldlr−/−) were fed a Western diet (high fat, high sucrose, high cholesterol) beginning one week prior to the start of treatments. XYM Ldlr−/− mice were then administered two different doses of Trop (10 or 20 mg/kg/day) by osmotic minipump for 7 days. The minipumps were then replaced with new pumps containing both AngII (1,000 ng/kg/min) and Trop and treatment was continued for 28 days.

Atherosclerosis was quantified en face in the aortic arch. Briefly, the entire length of the aorta was removed and the intimal surface exposed, in its entirety, by a longitudinal cut through the inner curvature of the aortic arch and down the anterior aspect of the remaining aorta. A cut is also made through the greater curvature of the aortic arch to the subclavian branch. The tissue is then pinned to a dark surface. Arch areas were defined by drawing a 3-mm line from the left subclavian artery. The intimal area of the aortic arch was defined as the region from the orifice of innominate artery to the orifice of the left subclavian artery. Thoracic areas were defined by drawing a 9 mm line from the end of the arch area to the diaphragm muscle. Atherosclerotic areas were quantified by drawing a line around the borders and summing the total area of each. Lesions were summed and divided by the total arch or thoracic area to calculate the percent lesion area. Measurements were performed using Nikon NIS-Elements Version 5.2.

Figure 23:
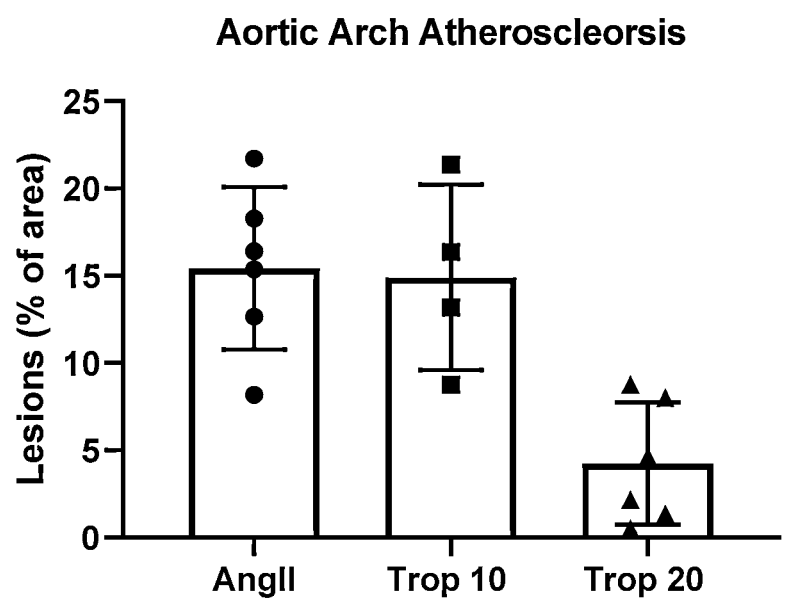
FIG. 23. Atherosclerosis of the aortic arch. Tropisetron at 20 mg/kg/day significantly reduce the formation of atherosclerotic plaque in the arch of the aorta (p<0.01).

Treatment with tropisetron (20 mg/kg/day) resulted in a reduction in the percent lesion surface area of the aortic arch of AngII-infused mice: 4.24±3.5 compared to 14.92±5.3 for tropisetron 10 mg/kg/day and 15.43±4.7 for AngII alone (FIG. 23). There was a similar reduction in atherosclerosis in the thoracic aortas of 20 mg/kg/day tropisetron treated mice compared to tropisetron at 10 mg/kg/day and AngII alone (7.43±7.95 for 20 mg/kg/day tropisetron; 14.14±6.4 for 10 mg/kg/day tropisetron; 13.37±4.5 for AngII only).

Example 14: 5HT3R Antagonist Treatment Reduces Serum Cholesterol and Serum Triglycerides Male mice (XYM Ldlr−/−) were fed a Western diet (high fat, high sucrose, high cholesterol) beginning one week prior to the start of treatments. XYM Ldlr−/− mice were then administered two different doses of Trop (10 or 20 mg/kg/day) by osmotic minipump for 7 days. The minipumps were then replaced with new pumps containing both AngII (1,000 ng/kg/min) and Trop and treatment was continued for 28 days. Concentrations of total serum cholesterol, triglycerides and free fatty acids were quantified (blood collected from cardiac puncture) using enzymatic assay kits.

Figure 24:
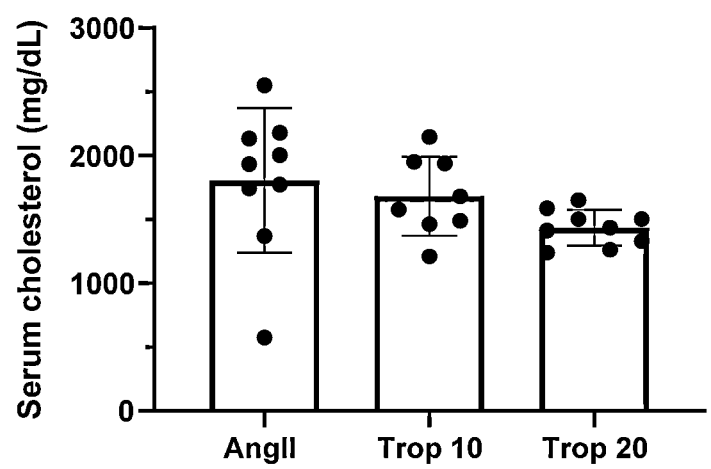
FIG. 24. Tropisetron reduces serum cholesterol in hypercholesterolemic mice.
Figure 25:
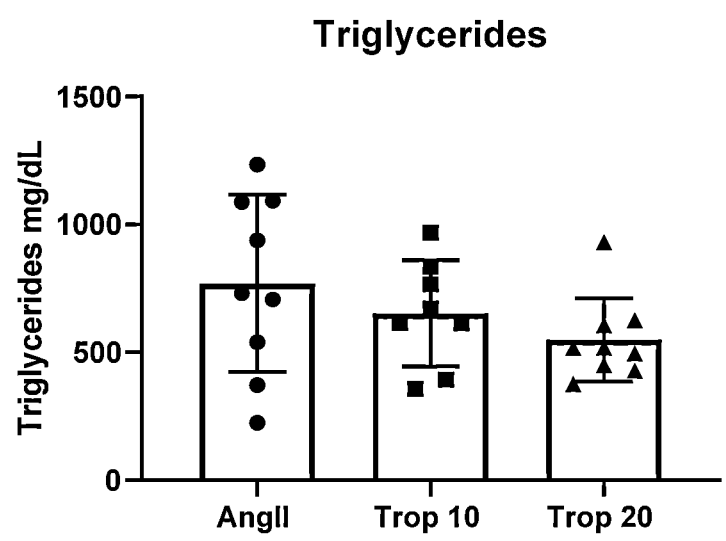
FIG. 25. Tropisetron reduces serum triglycerides in hypertriglyeridemic mice.

Tropisetron reduced serum cholesterol in a dose dependent manner (FIG. 24). Serum cholesterol levels were: AngII infused mice=1807±188.6, Trop 10=1683±109.5, and Trop 20=1437±46.7. Tropisetron also reduced serum triglycerides in a dose dependent manner (FIG. 25). Serum triglyceride levels were: AngII infused mice=770±115.7, Trop 10=652±73.6, and Trop 20=549±54.4.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Hannawa K K, Eliason J L and Upchurch G R, Jr. Gender differences in abdominal aortic aneurysms. Vascular. 2009; 17 Suppl 1:S30-9.
2. Makrygiannis G, Courtois A, Drion P, Defraigne J O, Kuivaniemi H and Sakalihasan N. Sex differences in abdominal aortic aneurysm: the role of sex hormones. Ann Vasc Surg. 2014; 28:1946-58.
3. Prakash S K and Milewicz D M. X Marks the Spot: The Profound Impact of Sex on Aortic Disease. Arterioscler Thromb Vasc Biol. 2018; 38:9-11.
4. Chung J C, Wong E, Tang M, Eliathamby D, Forbes T L, Butany J, Simmons C A and Ouzounian M. Biomechanics of Aortic Dissection: A Comparison of Aortas Associated With Bicuspid and Tricuspid Aortic Valves. Journal of the American Heart Association. 2020; 9:e016715.
5. Cheng Z J, Vapaatalo H and Mervaala E. Angiotensin II and vascular inflammation. Med Sci Monit. 2005; 11:RA194-205.
6. Lagrange J, Kossmann S and Wenzel P. Assessment of Vascular Dysfunction and Inflammation Induced by Angiotensin II in Mice. Methods Mol Biol. 2017; 1559:439-453.
7. Gavrila D, Li W G, McCormick M L, Thomas M, Daugherty A, Cassis L A, Miller F J, Jr., Oberley L W, Dellsperger K C and Weintraub N L. Vitamin E inhibits abdominal aortic aneurysm formation in angiotensin II-infused apolipoprotein E-deficient mice. Arterioscler Thromb Vasc Biol. 2005; 25:1671-7.
8. Saraff K, Babamusta F, Cassis L A and Daugherty A. Aortic dissection precedes formation of aneurysms and atherosclerosis in angiotensin II-infused, apolipoprotein E-deficient mice. Arterioscler Thromb Vasc Biol. 2003; 23:1621-6.
9. Alsiraj Y, Thatcher S E, Blalock E, Fleenor B, Daugherty A and Cassis L A. Sex Chromosome Complement Defines Diffuse Versus Focal Angiotensin II-Induced Aortic Pathology. Arterioscler Thromb Vasc Biol. 2018; 38:143-153.
10. Henriques T A, Huang J, D'Souza S S, Daugherty A and Cassis L A. Orchidectomy, but not ovariectomy, regulates angiotensin II-induced vascular diseases in apolipoprotein E-deficient mice. Endocrinology. 2004; 145:3866-72.
11. Henriques T, Zhang X, Yiannikouris F B, Daugherty A and Cassis L A. Androgen increases AT1a receptor expression in abdominal aortas to promote angiotensin II-induced AAAs in apolipoprotein E-deficient mice. Arterioscler Thromb Vasc Biol. 2008; 28:1251-6.
12. Zhang X, Thatcher S E, Rateri D L, Bruemmer D, Charnigo R, Daugherty A and Cassis L A. Transient exposure of neonatal female mice to testosterone abrogates the sexual dimorphism of abdominal aortic aneurysms. Circ Res. 2012; 110:e73-85.
13. Alsiraj Y, Thatcher S E, Charnigo R, Chen K, Blalock E, Daugherty A and Cassis L A. Female Mice With an XY Sex Chromosome Complement Develop Severe Angiotensin II-Induced Abdominal Aortic Aneurysms. Circulation. 2017; 135:379-391.
14. Itoh Y, Mackie R, Kampf K, Domadia S, Brown J D, O'Neill R and Arnold A P. Four core genotypes mouse model: localization of the Sry transgene and bioassay for testicular hormone levels. BMC Res Notes. 2015; 8:69.
15. Maricq A V, Peterson A S, Brake A J, Myers R M and Julius D. Primary structure and functional expression of the 5HT3 receptor, a serotonin-gated ion channel. Science. 1991; 254:432-7.
16. Hussy N, Lukas W and Jones K A. Functional properties of a cloned 5-hydroxytryptamine ionotropic receptor subunit: comparison with native mouse receptors. J Physiol. 1994; 481 (Pt 2):311-23.
17. Brown A M, Hope A G, Lambert J J and Peters J A. Ion permeation and conduction in a human recombinant 5-HT3 receptor subunit (h5-HT3A). J Physiol. 1998; 507 (Pt 3):653-65.
18. Zulkifli M H, Viswenaden P, Jasamai M, Azmi N and Yaakob N S. Potential roles of 5-HT3 receptor (5-HT3R) antagonists in modulating the effects of nicotine. Biomed Pharmacother. 2019; 112:108630.
19. Oakes J M, Fuchs R M, Gardner J D, Lazartigues E and Yue X. Nicotine and the renin-angiotensin system. Am J Physiol Regul Integr Comp Physiol. 2018; 315:R895-R906.
20. Li J M, Cui T X, Shiuchi T, Liu H W, Min L J, Okumura M, Jinno T, Wu L, Iwai M and Horiuchi M. Nicotine enhances angiotensin II-induced mitogenic response in vascular smooth muscle cells and fibroblasts. Arterioscler Thromb Vasc Biol. 2004; 24:80-4.
21. Clayton J A and Collins F S. Policy: NIH to balance sex in cell and animal studies. Nature. 2014; 509:282-3.
22. Sandberg K, Umans J G and Georgetown Consensus Conference Work G. Recommendations concerning the new U.S. National Institutes of Health initiative to balance the sex of cells and animals in preclinical research. FASEB J. 2015; 29:1646-52.
23. Komukai K, Mochizuki S and Yoshimura M. Gender and the renin-angiotensin-aldosterone system. Fundam Clin Pharmacol. 2010; 24:687-98.
24. Kang A K and Miller J A. Effects of gender on the renin-angiotensin system, blood pressure, and renal function. Curr Hypertens Rep. 2002; 4:143-51.
25. Sullivan J C. Sex and the renin-angiotensin system: inequality between the sexes in response to RAS stimulation and inhibition. Am J Physiol Regul Integr Comp Physiol. 2008; 294:R1220-6.
26. Hilliard L M, Sampson A K, Brown R D and Denton K M. The "his and hers" of the renin-angiotensin system. Curr Hypertens Rep. 2013; 15:71-9.
27. Maric C. Sex differences in cardiovascular disease and hypertension: involvement of the renin-angiotensin system. Hypertension. 2005; 46:475-6.
28. Fischer M, Baessler A and Schunkert H. Renin angiotensin system and gender differences in the cardiovascular system. Cardiovasc Res. 2002; 53:672-7.
29. Song J, Kost C K, Jr. and Martin D S. Androgens potentiate renal vascular responses to angiotensin II via amplification of the Rho kinase signaling pathway. Cardiovasc Res. 2006; 72:456-63.

30. Kang N N, Fu L, Xu J, Han Y, Cao J X, Sun J F and Zheng M. Testosterone improves cardiac function and alters angiotensin II receptors in isoproterenol-induced heart failure. Arch Cardiovasc Dis. 2012; 105:68-76.
31. Nickenig G, Baumer A T, Grohe C, Kahlert S, Strehlow K, Rosenkranz S, Stablein A, Beckers F, Smits J F, Daemen M J, Vetter H and Bohm M. Estrogen modulates AT1 receptor gene expression in vitro and in vivo. Circulation. 1998; 97:2197-201.
32. Krishnamurthi K, Verbalis J G, Zheng W, Wu Z, Clerch L B and Sandberg K. Estrogen regulates angiotensin AT1 receptor expression via cytosolic proteins that bind to the 5' leader sequence of the receptor mRNA. Endocrinology. 1999; 140:5435-8.
33. Kisley L R, Sakai R R and Fluharty S J. Estrogen decreases hypothalamic angiotensin II AT1 receptor binding and mRNA in the female rat. Brain Res. 1999; 844:34-42.
34. Nickenig G, Strehlow K, Wassmann S, Baumer A T, Albory K, Sauer H and Bohm M. Differential effects of estrogen and progesterone on AT(1) receptor gene expression in vascular smooth muscle cells. Circulation. 2000; 102:1828-33.
35. Gupte M, Boustany-Kari C M, Bharadwaj K, Police S, Thatcher S, Gong M C, English V L and Cassis L A. ACE2 is expressed in mouse adipocytes and regulated by a high-fat diet. Am J Physiol Regul Integr Comp Physiol. 2008; 295:R781-8.
36. Shoemaker R, Tannock L R, Su W, Gong M, Gurley S B, Thatcher S E, Yiannikouris F, Ensor C M and Cassis L A. Adipocyte deficiency of ACE2 increases systolic blood pressures of obese female C57BL/6 mice. Biol Sex Differ. 2019; 10:45.
37. Wang Y, Shoemaker R, Thatcher S E, Batifoulier-Yiannikouris F, English V L and Cassis L A. Administration of 17beta-estradiol to ovariectomized obese female mice reverses obesity-hypertension through an ACE2-dependent mechanism. American journal of physiology Endocrinology and metabolism. 2015; 308:E1066-75.
38. AlSiraj Y, Chen X, Thatcher S E, Temel R E, Cai L, Blalock E, Katz W, Ali H M, Petriello M, Deng P, Morris A J, Wang X, Lusis A J, Arnold A P, Reue K, Thompson K, Tso P and Cassis L A. XX sex chromosome complement promotes atherosclerosis in mice. Nat Commun. 2019; 10:2631.
39. Thatcher S E, Zhang X, Woody S, Wang Y, Alsiraj Y, Charnigo R, Daugherty A and Cassis L A. Exogenous 17-β estradiol administration blunts progression of established angiotensin II-induced abdominal aortic aneurysms in female ovariectomized mice. Biol Sex Differ. 2015; 6:12.
40. Skuse D H. X-linked genes and mental functioning. Hum Mol Genet. 2005; 14 Spec No 1:R27-32.
41. Laumonnier F, Cuthbert P C and Grant S G. The role of neuronal complexes in human X-linked brain diseases. Am J Hum Genet. 2007; 80:205-20.
42. Crackower M A, Sarao R, Oudit G Y, Yagil C, Kozieradzki I, Scanga S E, Oliveira-dos-Santos A J, da Costa J, Zhang L, Pei Y, Scholey J, Ferrario C M, Manoukian A S, Chappell M C, Backx P H, Yagil Y and Penninger J M. Angiotensin-converting enzyme 2 is an essential regulator of heart function. Nature. 2002; 417:822-8.
43. Hein L, Dzau V J and Barsh G S. Linkage mapping of the angiotensin AT2 receptor gene (Agtr2) to the mouse X chromosome. Genomics. 1995; 30:369-71.
44. Koike G, Winer E S, Horiuchi M, Brown D M, Szpirer C, Dzau V J and Jacob H J. Cloning, characterization, and genetic mapping of the rat type 2 angiotensin II receptor gene. Hypertension. 1995; 26:998-1002.
45. Ji H, Zheng W, Wu X, Liu J, Ecelbarger C M, Watkins R, Arnold A P and Sandberg K. Sex chromosome effects unmasked in angiotensin II-induced hypertension. Hypertension. 2010; 55:1275-82.
46. Fuchs U. Scanning electron microscopy of the aorta. Prog Biochem Pharmacol. 1977; 13:182-4.
47. Owens G K. Influence of blood pressure on development of aortic medial smooth muscle hypertrophy in spontaneously hypertensive rats. Hypertension. 1987; 9:178-87.
48. Geisterfer A A, Peach M J and Owens G K. Angiotensin II induces hypertrophy, not hyperplasia, of cultured rat aortic smooth muscle cells. Circ Res. 1988; 62:749-56.
49. Berk B C, Vekshtein V, Gordon H M and Tsuda T. Angiotensin II-stimulated protein synthesis in cultured vascular smooth muscle cells. Hypertension. 1989; 13:305-14.
50. Clozel M, Kuhn H, Hefti F and Baumgartner H R. Endothelial dysfunction and subendothelial monocyte macrophages in hypertension. Effect of angiotensin converting enzyme inhibition. Hypertension. 1991; 18:13-241.
51. Griendling K K, Minieri C A, Ollerenshaw J D and Alexander R W. Angiotensin II stimulates NADH and NADPH oxidase activity in cultured vascular smooth muscle cells. Circ Res. 1994; 74:1141-8.
52. Laursen J B, Rajagopalan S, Galis Z, Tarpey M, Freeman B A and Harrison D G. Role of superoxide in angiotensin II-induced but not catecholamine-induced hypertension. Circulation. 1997; 95:588-93.
53. Dupont L J, Pype J L, Meade C J, DeLeyn P, Deneffe G, Demedts M G and Verleden G M. Epinastine (WAL 801CL) inhibits the electrical field stimulation-induced cholinergic contraction in guinea pig and human airways in vitro. Eur Respir J. 1999; 14:1068-75.
54. Nishijo N, Sugiyama F, Kimoto K, Taniguchi K, Murakami K, Suzuki S, Fukamizu A and Yagami K. Salt-sensitive aortic aneurysm and rupture in hypertensive transgenic mice that overproduce angiotensin II. Lab Invest. 1998; 78:1059-66.
55. Kim D K, Huh J E, Lee S H, Hong K P, Park J E, Seo J D and Lee W R. Angiotensin II stimulates proliferation of adventitial fibroblasts cultured from rat aortic explants. J Korean Med Sci. 1999; 14:487-96.
56. Daugherty A, Manning M W and Cassis L A. Angiotensin II promotes atherosclerotic lesions and aneurysms in apolipoprotein E-deficient mice. J Clin Invest. 2000; 105:1605-12.
57. Weiss D, Kools J J and Taylor W R. Angiotensin II-induced hypertension accelerates the development of atherosclerosis in apoE-deficient mice. Circulation. 2001; 103:448-54.
58. Dol F, Martin G, Staels B, Mares A M, Cazaubon C, Nisato D, Bidouard J P, Janiak P, Schaeffer P and Herbert J M. Angiotensin AT1 receptor antagonist irbesartan decreases lesion size, chemokine expression, and macrophage accumulation in apolipoprotein E-deficient mice. J Cardiovasc Pharmacol. 2001; 38:395-405.
59. Tham D M, Martin-McNulty B, Wang Y X, Da Cunha V, Wilson D W, Athanassious C N, Powers A F, Sullivan M E and Rutledge J C. Angiotensin II injures the arterial wall causing increased aortic stiffening in apolipoprotein E-deficient mice. Am J Physiol Regul Integr Comp Physiol. 2002; 283:R1442-9.
60. Ceiler D L, Nelissen-Vrancken H J, Smits J F and De Mey J G. Pressure but not angiotensin II-induced increases in wall mass or tone influences static and dynamic aortic mechanics. J Hypertens. 1999; 17:1109-16.
61. Favreau J T, Nguyen B T, Gao I, Yu P, Tao M, Schneiderman J, Gaudette G R and Ozaki C K. Murine ultrasound imaging for circumferential strain analyses in the angiotensin II abdominal aortic aneurysm model. J Vasc Surg. 2012; 56:462-9.
62. Haskett D, Speicher E, Fouts M, Larson D, Azhar M, Utzinger U and Vande Geest J. The effects of angiotensin II on the coupled microstructural and biomechanical response of C57BL/6 mouse aorta. J Biomech. 2012; 45:772-9.
63. Eagleton M J, Ballard N, Lynch E, Srivastava S D, Upchurch G R, Jr. and Stanley J C. Early increased MT1-MMP expression and late MMP-2 and MMP-9 activity during Angiotensin II induced aneurysm formation. J Surg Res. 2006; 135:345-51.
64. Manning M W, Cassis L A and Daugherty A. Differential effects of doxycycline, a broad-spectrum matrix metalloproteinase inhibitor, on angiotensin II-induced atherosclerosis and abdominal aortic aneurysms. Arterioscler Thromb Vasc Biol. 2003; 23:483-8.
65. Gershon M D and Ross L L. Location of sites of 5-hydroxytryptamine storage and metabolism by radioautography. J Physiol. 1966; 186:477-92.
66. Ayala-Lopez N, Martini M, Jackson W F, Dartos E, Burnett R, Seitz B, Fink G D and Watts S W. Perivascular adipose tissue contains functional catecholamines. Pharmacol Res Perspect. 2014; 2:e00041.
67. Crane J D, Palanivel R, Mottillo E P, Bujak A L, Wang H, Ford R J, Collins A, Blumer R M, Fullerton M D, Yabut J M, Kim J J, Ghia J E, Hamza S M, Morrison K M, Schertzer J D, Dyck J R, Khan W I and Steinberg G R. Inhibiting peripheral serotonin synthesis reduces obesity and metabolic dysfunction by promoting brown adipose tissue thermogenesis. Nat Med. 2015; 21:166-72.
68. Oh C M, Namkung J, Go Y, Shong K E, Kim K, Kim H, Park B Y, Lee H W, Jeon Y H, Song J, Shong M, Yadav V K, Karsenty G, Kajimura S, Lee I K, Park S and Kim H. Regulation of systemic energy homeostasis by serotonin in adipose tissues. Nat Commun. 2015; 6:6794.
69. Matsuda M, Imaoka T, Vomachka A J, Gudelsky G A, Hou Z, Mistry M, Bailey J P, Nieport K M, Walther D J, Bader M and Horseman N D. Serotonin regulates mammary gland development via an autocrine-paracrine loop. Dev Cell. 2004; 6:193-203.
70. Kim H, Toyofuku Y, Lynn F C, Chak E, Uchida T, Mizukami H, Fujitani Y, Kawamori R, Miyatsuka T, Kosaka Y, Yang K, Honig G, van der Hart M, Kishimoto N, Wang J, Yagihashi S, Tecott L H, Watada H and German M S. Serotonin regulates pancreatic beta cell mass during pregnancy. Nat Med. 2010; 16:804-8.
71. Ohara-Imaizumi M, Kim H, Yoshida M, Fujiwara T, Aoyagi K, Toyofuku Y, Nakamichi Y, Nishiwaki C, Okamura T, Uchida T, Fujitani Y, Akagawa K, Kakei M, Watada H, German M S and Nagamatsu S. Serotonin regulates glucose-stimulated insulin secretion from pancreatic beta cells during pregnancy. Proc Natl Acad Sci USA. 2013; 110:19420-5.
72. Davila D and Davila T. Effect of angiotensin II and its analogs on uptake and release of 14C-5-hydroxytryptamine by rat brain. Eur J Pharmacol. 1975; 34:329-35.
73. Nahmod V E, Finkielman S, Benarroch E E and Pirola C J. Angiotensin regulates release and synthesis of serotonin in brain. Science. 1978; 202:1091-3.
74. Braszko J J, Majewski K, Maciejewski A and Wisniewski K. Effect of angiotensin II on some behavioral and neurochemical measures of the central serotonine system. Biomed Biochim Acta. 1985; 44:1359-68.
75. Mendelsohn F A, Jenkins T A and Berkovic S F. Effects of angiotensin II on dopamine and serotonin turnover in the striatum of conscious rats. Brain Res. 1993; 613:221-9.
76. Tanaka J, Kariya K and Nomura M. Angiotensin II reduces serotonin release in the rat subfornical organ area. Peptides. 2003; 24:881-7.
77. Gilmore B and Michael M. Treatment of acute migraine headache. Am Fam Physician. 2011; 83:271-80.
78. Mylecharane E J. Mechanisms involved in serotonin-induced vasodilatation. Blood Vessels. 1990; 27:116-26.
79. Woodman O L and Dusting G J. Involvement of nitric oxide in coronary vascular responses to 5-hydroxytryptamine in the anaesthetized greyhound. Clin Exp Pharmacol Physiol. 1994; 21:377-81.
80. Ellis E S, Byrne C, Murphy O E, Tilford N S and Baxter G S. Mediation by 5-hydroxytryptamine2B receptors of endothelium-dependent relaxation in rat jugular vein. Br J Pharmacol. 1995; 114:400-4.
81. Watts S W, Morrison S F, Davis R P and Barman S M. Serotonin and blood pressure regulation. Pharmacol Rev. 2012; 64:359-88.
82. Thompson A J, Padgett C L and Lummis S C. Mutagenesis and molecular modeling reveal the importance of the 5-HT3 receptor F-loop. J Biol Chem. 2006; 281: 16576-82.
83. Walstab J, Rappold G and Niesler B. 5-HT(3) receptors: role in disease and target of drugs. Pharmacology & therapeutics. 2010; 128:146-69.
84. Derkach V, Surprenant A and North R A. 5-HT3 receptors are membrane ion channels. Nature. 1989; 339:706-9.
85. Barnes J M, Barnes N M, Costall B, Ironside J W and Naylor R J. Identification and characterisation of 5-hydroxytryptamine 3 recognition sites in human brain tissue. J Neurochem. 1989; 53:1787-93.
86. Abi-Dargham A, Laruelle M, Wong D T, Robertson D W, Weinberger D R and Kleinman J E. Pharmacological and regional characterization of [3H]LY278584 binding sites in human brain. J Neurochem. 1993; 60:730-7.
87. Okubo M, Satoh Y, Hirakawa M, Sasaki K, Masu K, G J M, Ikeda-Kurosawa C, Kurosaka D and Saino T. Different effect of serotonin on intracellular calcium ion dynamics in the smooth muscle cells between rat posterior ciliary artery and vorticose vein. Biomed Res. 2016; 37:101-15.
88. Mazzia C, Hicks G A and Clerc N. Neuronal location of 5-hydroxytryptamine3 receptor-like immunoreactivity in the rat colon. Neuroscience. 2003; 116:1033-41.
89. Kamato T, Ito H, Suzuki T, Miyata K and Honda K. Studies on serotonin (5-HT)3-receptor antagonist effects of enantiomers of 4,5,6,7-tetrahydro-1H-benzimidazole derivatives. Jpn J Pharmacol. 1995; 67:185-94.
90. Matsumoto-Miyai K, Yoshizumi M and Kawatani M. Regulatory Effects of 5-Hydroxytryptamine Receptors on Voiding Function. Adv Ther. 2015; 32 Suppl 1:3-15.
91. Bhattacharya A, Dang H, Zhu Q M, Schnegelsberg B, Rozengurt N, Cain G, Prantil R, Vorp D A, Guy N, Julius D, Ford A P, Lester H A and Cockayne D A. Uropathic observations in mice expressing a constitutively active point mutation in the 5-HT3A receptor subunit. J Neurosci. 2004; 24:5537-48.
92. Idzko M, Panther E, Stratz C, Muller T, Bayer H, Zissel G, Durk T, Sorichter S, Di Virgilio F, Geissler M, Fiebich B, Herouy Y, Elsner P, Norgauer J and Ferrari D. The serotoninergic receptors of human dendritic cells: identification and coupling to cytokine release. Journal of immunology. 2004; 172:6011-9.
93. Rahimi R, Nikfar S and Abdollahi M. Efficacy and tolerability of alosetron for the treatment of irritable bowel syndrome in women and men: a meta-analysis of eight randomized, placebo-controlled, 12-week trials. Clin Ther. 2008; 30:884-901.
94. Bhatnagar S, Nowak N, Babich L and Bok L. Deletion of the 5-HT3 receptor differentially affects behavior of males and females in the Porsolt forced swim and defensive withdrawal tests. Behav Brain Res. 2004; 153:527-35.
95. Balasuriya G K, Hill-Yardin E L, Gershon M D and Bornstein J C. A sexually dimorphic effect of cholera toxin: rapid changes in colonic motility mediated via a 5-HT3 receptor-dependent pathway in female C57Bl/6 mice. J Physiol. 2016; 594:4325-38.
96. El-Ayache N and Galligan J J. 5-HT3 receptor signaling in serotonin transporter-knockout rats: a female sex-specific animal model of visceral hypersensitivity. Am J Physiol Gastrointest Liver Physiol. 2019; 316:G132-G143.
97. Sine S M and Engel A G. Recent advances in Cys-loop receptor structure and function. Nature. 2006; 440:448-55.
98. Lester R A. Activation and desensitization of heteromeric neuronal nicotinic receptors: implications for non-synaptic transmission. Bioorg Med Chem Lett. 2004; 14:1897-900.
99. Shen J X and Yakel J L. Nicotinic acetylcholine receptor-mediated calcium signaling in the nervous system. Acta Pharmacol Sin. 2009; 30:673-80.
100. Dani J A and Bertrand D. Nicotinic acetylcholine receptors and nicotinic cholinergic mechanisms of the central nervous system. Annu Rev Pharmacol Toxicol. 2007; 47:699-729.
101. Ribeiro E B, Bettiker R L, Bogdanov M and Wurtman R J. Effects of systemic nicotine on serotonin release in rat brain. Brain Res. 1993; 621:311-8.
102. Mihailescu S, Palomero-Rivero M, Meade-Huerta P, Maza-Flores A and Drucker-Colin R. Effects of nicotine and mecamylamine on rat dorsal raphe neurons. Eur J Pharmacol. 1998; 360:31-6.
103. Galindo-Charles L, Hernandez-Lopez S, Galarraga E, Tapia D, Bargas J, Garduno J, Frias-Dominguez C, Drucker-Colin R and Mihailescu S. Serotoninergic dorsal raphe neurons possess functional postsynaptic nicotinic acetylcholine receptors. Synapse. 2008; 62:601-15.
104. Hernandez-Vazquez F, Chavarria K, Garduno J, Hernandez-Lopez S and Mihailescu S P. Nicotine increases GABAergic input on rat dorsal raphe serotonergic neurons through alpha7 nicotinic acetylcholine receptor. J Neurophysiol. 2014; 112:3154-63.
105. Adler I and Hensel O. Intravenous Injections of Nicotine and their effects upon the Aorta of Rabbits. J Med Res. 1906; 15:229-240 5.
106. Millson D R. Nicotine and the effect of antisympathomimetic agents on the aorta of the rabbit. Br J Pharmacol Chemother. 1959; 14:239-42.
107. Kokubu T and Pollak O J. Influence of nicotine on cells of rabbits' aorta and myocardium in tissue cultures. Exp Mol Pathol. 1962; 1:293-303.
108. Stefanovich V, Gore I, Kajiyama G and Iwanaga Y. The effect of nicotine on dietary atherogenesis in rabbits. Exp Mol Pathol. 1969; 11:71-81.
109. Alster P and Wennmalm A. Effect of nicotine on prostacyclin formation in rat aorta. Eur J Pharmacol. 1983; 86:441-6.
110. Bull H A, Pittilo R M, Blow D J, Blow C M, Rowles P M, Woolf N and Machin S J. The effects of nicotine on PGI2 production by rat aortic endothelium. Thromb Haemost. 1985; 54:472-4.
111. Chahine R, Calderone A and Navarro-Delmasure C. The in vitro effects of nicotine and cotinine on prostacyclin and thromboxane biosynthesis. Prostaglandins Leukot Essent Fatty Acids. 1990; 40:261-6.
112. Lin S J, Hong C Y, Chang M S, Chiang B N and Chien S. Long-term nicotine exposure increases aortic endothelial cell death and enhances transendothelial macromolecular transport in rats. Arterioscler Thromb. 1992; 12:1305-12.
113. Cucina A, Corvino V, Sapienza P, Borrelli V, Lucarelli M, Scarpa S, Strom R, Santoro-D'Angelo L and Cavallaro A. Nicotine regulates basic fibroblastic growth factor and transforming growth factor beta1 production in endothelial cells. Biochem Biophys Res Commun. 1999; 257: 306-12.
114. Tonnessen B H, Severson S R, Hurt R D and Miller V M. Modulation of nitric-oxide synthase by nicotine. J Pharmacol Exp Ther. 2000; 295:601-6.
115. Carty C S, Huribal M, Marsan B U, Ricotta J J and Dryjski M. Nicotine and its metabolite cotinine are mitogenic for human vascular smooth muscle cells. J Vasc Surg. 1997; 25:682-8.
116. Nordskog B K, Blixt A D, Morgan W T, Fields W R and Hellmann G M. Matrix-degrading and pro-inflammatory changes in human vascular endothelial cells exposed to cigarette smoke condensate. Cardiovasc Toxicol. 2003; 3:101-17.
117. Jacob-Ferreira A L, Passos C J, Gerlach R F, Barbosa F, Jr. and Tanus-Santos J E. A functional matrix metalloproteinase (MMP)-9 polymorphism modifies plasma MMP-9 levels in subjects environmentally exposed to mercury. Sci Total Environ. 2010; 408:4085-92.
118. Gu Z, Fonseca V and Hai C M. Nicotinic acetylcholine receptor mediates nicotine-induced actin cytoskeletal remodeling and extracellular matrix degradation by vascular smooth muscle cells. Vascul Pharmacol. 2013; 58:87-97.
119. Wang Z, Liu B, Zhu J, Wang D and Wang Y. Nicotine-mediated autophagy of vascular smooth muscle cell accelerates atherosclerosis via nAChRs/ROS/NF-kappaB signaling pathway. Atherosclerosis. 2019; 284:1-10.
120. Yoshiyama S, Chen Z, Okagaki T, Kohama K, Nasu-Kawaharada R, Izumi T, Ohshima N, Nagai T and Nakamura A. Nicotine exposure alters human vascular smooth muscle cell phenotype from a contractile to a synthetic type. Atherosclerosis. 2014; 237:464-70.
121. Wang Y, Zhang F, Yang W and Xue S. Nicotine induces pro-inflammatory response in aortic vascular smooth muscle cells through a NFkappaB/osteopontin amplification loop-dependent pathway. Inflammation. 2012; 35:342-9.
122. Kugo H, Zaima N, Tanaka H, Urano T, Unno N and Moriyama T. The effects of nicotine administration on the pathophysiology of rat aortic wall. Biotech Histochem. 2017; 92:141-148.
123. Adamopoulos D, Argacha J F, Gujic M, Preumont N, Degaute J P and van de Borne P. Acute effects of nicotine on arterial stiffness and wave reflection in healthy young non-smokers. Clin Exp Pharmacol Physiol. 2009; 36:784-9.

124. Kim J W, Park C G, Hong S J, Park S M, Rha S W, Seo H S, Oh D J and Rho Y M. Acute and chronic effects of cigarette smoking on arterial stiffness. Blood Press. 2005; 14:80-5.
125. Norman P E and Curci J A. Understanding the effects of tobacco smoke on the pathogenesis of aortic aneurysm. Arterioscler Thromb Vasc Biol. 2013; 33:1473-7.
126. Jahangir E, Lipworth L, Edwards T L, Kabagambe E K, Mumma M T, Mensah G A, Fazio S, Blot W J and Sampson U K. Smoking, sex, risk factors and abdominal aortic aneurysms: a prospective study of 18 782 persons aged above 65 years in the Southern Community Cohort Study. J Epidemiol Community Health. 2015; 69:481-8.
127. Wang S, Zhang C, Zhang M, Liang B, Zhu H, Lee J, Viollet B, Xia L, Zhang Y and Zou M H. Activation of AMP-activated protein kinase alpha2 by nicotine instigates formation of abdominal aortic aneurysms in mice in vivo. Nat Med. 2012; 18:902-10.
128. Maegdefessel L, Azuma J, Toh R, Deng A, Merk D R, Raiesdana A, Leeper N J, Raaz U, Schoelmerich A M, McConnell M V, Dalman R L, Spin J M and Tsao P S. MicroRNA-21 blocks abdominal aortic aneurysm development and nicotine-augmented expansion. Sci Transl Med. 2012; 4:122ra22.
129. Wagenhauser M U, Schellinger I N, Yoshino T, Toyama K, Kayama Y, Deng A, Guenther S P, Petzold A, Mulorz J, Mulorz P, Hasenfuss G, Ibing W, Elvers M, Schuster A, Ramasubramanian A K, Adam M, Schelzig H, Spin J M, Raaz U and Tsao P S. Chronic Nicotine Exposure Induces Murine Aortic Remodeling and Stiffness Segmentation-Implications for Abdominal Aortic Aneurysm Susceptibility. Front Physiol. 2018; 9:1459.
130. Guo Z Z, Cao Q A, Li Z Z, Liu L P, Zhang Z, Zhu Y J, Chu G and Dai Q Y. SP600125 Attenuates Nicotine-Related Aortic Aneurysm Formation by Inhibiting Matrix Metalloproteinase Production and CC Chemokine-Mediated Macrophage Migration. Mediators Inflamm. 2016; 2016:9142425.
131. Liu J, Sawada H, Howatt D A, Moorleghen J J, Vsevolozhskaya O, Daugherty A and Lu H S. Hypercholesterolemia Accelerates Both the Initiation and Progression of Angiotensin II-induced Abdominal Aortic Aneurysms. Ann Vasc Med Res. 2020; 6.
132. Liu J, Lu H, Howatt D A, Balakrishnan A, Moorleghen J J, Sorci-Thomas M, Cassis L A and Daugherty A. Associations of ApoAI and ApoB-containing lipoproteins with AngII-induced abdominal aortic aneurysms in mice. Arterioscler Thromb Vasc Biol. 2015; 35:1826-34.
133. Arnold A P and Chen X. What does the "four core genotypes" mouse model tell us about sex differences in the brain and other tissues? Front Neuroendocrinol. 2009; 30:1-9.
134. De Vries G J, Rissman E F, Simerly R B, Yang L Y, Scordalakes E M, Auger C J, Swain A, Lovell-Badge R, Burgoyne P S and Arnold A P. A model system for study of sex chromosome effects on sexually dimorphic neural and behavioral traits. J Neurosci. 2002; 22:9005-14.
135. Burgoyne P S, Mahadevaiah S K, Perry J, Palmer S J and Ashworth A. The Y* rearrangement in mice: new insights into a perplexing PAR. Cytogenet Cell Genet. 1998; 80:37-40.
136. Richardson B P, Engel G, Donatsch P and Stadler P A. Identification of serotonin M-receptor subtypes and their specific blockade by a new class of drugs. Nature. 1985; 316:126-31.
137. Drisdel R C, Sharp D, Henderson T, Hales T G and Green W N. High affinity binding of epibatidine to serotonin type 3 receptors. J Biol Chem. 2008; 283:9659-65.
138. Zhang X, Thatcher S, Wu C, Daugherty A and Cassis L A. Castration of male mice prevents the progression of established angiotensin II-induced abdominal aortic aneurysms. J Vasc Surg. 2015; 61:767-76.
139. Yang J. Ion permeation through 5-hydroxytryptamine-gated channels in neuroblastoma N18 cells. J Gen Physiol. 1990; 96:1177-98.
140. Downie D L, Hope A G, Lambert J J, Peters J A, Blackburn T P and Jones B J. Pharmacological characterization of the apparent splice variants of the murine 5-HT3 R-A subunit expressed in Xenopus laevis oocytes. Neuropharmacology. 1994; 33:473-82.
141. Thompson A J, Chau P L, Chan S L and Lummis S C. Unbinding pathways of an agonist and an antagonist from the 5-HT3 receptor. Biophys J. 2006; 90:1979-91.
142. Wang Y, Shoemaker R, Powell D, Su W, Thatcher S and Cassis L. Differential effects of Mas receptor deficiency on cardiac function and blood pressure in obese male and female mice. Am J Physiol Heart Circ Physiol. 2017; 312:H459-H468.
143. Chignalia A Z, Schuldt E Z, Camargo L L, Montezano A C, Callera G E, Laurindo F R, Lopes L R, Avellar M C, Carvalho M R, Fortes Z B, Touyz R M and Tostes R C. Testosterone induces vascular smooth muscle cell migration by NADPH oxidase and c-Src-dependent pathways. Hypertension. 2012; 59:1263-71.
144. Thatcher S E, Zhang X, Woody S, Wang Y, Alsiraj Y, Charnigo R, Daugherty A and Cassis L A. Exogenous 17-beta estradiol administration blunts progression of established angiotensin II-induced abdominal aortic aneurysms in female ovariectomized mice. Biol Sex Differ. 2015; 6:12.
145. Quintana R A and Taylor W R. Cellular Mechanisms of Aortic Aneurysm Formation. Circ Res. 2019; 124:607-618.
146. Shen Y H, LeMaire S A, Webb N R, Cassis L A, Daugherty A and Lu H S. Aortic Aneurysms and Dissections Series: Part II: Dynamic Signaling Responses in Aortic Aneurysms and Dissections. Arterioscler Thromb Vasc Biol. 2020; 40:e78-e86.
147. Lu H, Cassis L A, Kooi C W and Daugherty A. Structure and functions of angiotensinogen. Hypertension research: official journal of the Japanese Society of Hypertension. 2016; 39:492-500.
148. Lu H, Howatt D A, Balakrishnan A, Graham M J, Mullick A E and Daugherty A. Hypercholesterolemia Induced by a PCSK9 Gain-of-Function Mutation Augments Angiotensin II-Induced Abdominal Aortic Aneurysms in C57BL/6 Mice-Brief Report. Arterioscler Thromb Vasc Biol. 2016; 36:1753-7.
149. Police S B, Thatcher S E, Charnigo R, Daugherty A and Cassis L A. Obesity promotes inflammation in periaortic adipose tissue and angiotensin II-induced abdominal aortic aneurysm formation. Arterioscler Thromb Vasc Biol. 2009; 29:1458-64.
150. Yu L, Bao L, Guo Y and Guo X. Determination of tropisetron in human plasma by high performance liquid chromatographic method with UV detection and its application to a bioequivalence study. J Chromatogr B Analyt Technol Biomed Life Sci. 2007; 846:20-3.
151. Stegbauer J, Thatcher S E, Yang G, Bottermann K, Rump L C, Daugherty A and Cassis L A. Mas receptor deficiency augments angiotensin II-induced atherosclerosis and aortic aneurysm ruptures in hypercholesterolemic male mice. J Vasc Surg. 2019; 70:1658-1668 e1.
152. Bauer S, Stormer E, Kaiser R, Tremblay P B, Brockmoller J and Roots I. Simultaneous determination of ondansetron and tropisetron in human plasma using HPLC with UV detection. Biomed Chromatogr. 2002; 16:187-90.
153. Kaisar M A, Kallem R R, Sajja R K, Sifat A E and Cucullo L. A convenient UHPLC-MS/MS method for routine monitoring of plasma and brain levels of nicotine and cotinine as a tool to validate newly developed preclinical smoking model in mouse. BMC Neurosci. 2017; 18:71.
154. Siu E C and Tyndale R F. Characterization and comparison of nicotine and cotinine metabolism in vitro and in vivo in DBA/2 and C57BL/6 mice. Mol Pharmacol. 2007; 71:826-34.
155. Russell M A, Jarvis M, Iyer R and Feyerabend C. Relation of nicotine yield of cigarettes to blood nicotine concentrations in smokers. Br Med J. 1980; 280:972-6.
156. Wada T, Naito M, Kenmochi H, Tsuneki H and Sasaoka T. Chronic nicotine exposure enhances insulin-induced mitogenic signaling via up-regulation of alpha7 nicotinic receptors in isolated rat aortic smooth muscle cells. Endocrinology. 2007; 148:790-9.
157. Alsiraj Y, Thatcher S E, Blalock E, Saintilord W N, Daugherty A, Lu H S, Luo W, Shen Y H, LeMaire S A, Arnold A P, Cassis L A. Monosomy X in female mice influences the regional foramtion and augments the severity of angiotensin II-induced aortopathies. Arterioscler Thromb Vasc Biol, in press, 2020.
158. Gregory R E and Ettinger D S. 5-HT3 receptor antagonists for the prevention of chemotherapy-induced nausea and vomiting. A comparison of their pharmacology and clinical efficacy. Drugs. 1998; 55:173-89.
160. Centers for Disease Control and Prevention, National Center for Health Statistics. Underlying Cause of Death 1999-2018 on CDC WONDER Online Database website. wonder.cdc.gov/ucd-icd10.html.
161. Bozzani A, Arici V, Franciscone M, Ticozzelli G, Sterpetti A V, and Ragni F. COVID-19 patients with abdominal aortic aneurysm may be at higher risk for sudden enlargement and rupture. J. Vascular Surgery. 2021; 75:387-388. doi.org/10.1016/j.jvs.2021.10.003.
162. Yamakuni H, Sawai H, Maeda Y, Imazumi K, Sakuma H, Matsuo M, Seitaro M, and Seki J. Probable Involvement of the 5-Hydroxytrytamine4 Receptor in Methotrexate-Induced Delayed Emesis in Dogs. J. Pharmacology and Experimental Therapeutics. 2000; 292(3):1002-1007.
163. Pahwa R, Jialal I. Atherosclerosis. [Updated 2021 Sep. 28]. In: StatPearls [Internet]. Treasure Island (FL): StatPearls Publishing; 2022 January. Available from: www.ncbi.nlm.nih.gov/books/NBK507799/
164. International Patent Application Publication No. WO 2009/033305 to Trenk, et al.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of treating or reducing risk of aneurysm, comprising: administering to a subject in need of such treatment or reduction of risk of aneurysm an effective amount of a $5HT_3R$ antagonist or pharmaceutically-acceptable salt thereof.

2. The method of claim 1, wherein the subject is identified as being at risk of aneurysm.

3. The method of claim 1, wherein the subject is identified as having an aneurysm.

4. The method of claim 1, wherein the subject is has a history of nicotine use.

5. The method of claim 1, wherein the subject is identified as having hypercholesterolemia.

6. The method of claim 1, wherein the subject is identified as having hypertriglyceridemia.

7. The method of claim 1, wherein the subject is identified as having atherosclerotic plaque.

8. The method of claim 1, wherein $5HT_3R$ antagonist is selected from the group consisting of: tropisetron, dolasetron, granisetron, ondansetron, palonosetron, and ramosetron.

9. A method of reducing cardiovascular risk, comprising: administering to a subject in need of such reduction of cardiovascular risk an effective amount of a $5HT_3R$ antagonist or pharmaceutically-acceptable salt thereof.

10. The method of claim 9, wherein the cardiovascular risk is nicotine-induced and/or the subject has a history of nicotine use.

11. The method of claim 9, wherein the subject is identified as being at risk of aneurysm.

12. The method of claim 9, wherein the subject is identified as having an aneurysm.

13. The method of claim 9, wherein the subject is identified as having hypercholesterolemia.

14. The method of claim 9, wherein the subject is identified as having hypertriglyceridemia.

15. The method of claim 9, wherein the subject is identified as having atherosclerotic plaque.

16. The method of claim 9, wherein $5HT_3R$ antagonist is selected from the group consisting of: tropisetron, dolasetron, granisetron, ondansetron, palonosetron, and ramosetron.

17. A method of reducing serum cholesterol, reducing serum triglycerides, and/or reducing atherosclerotic plaque, comprising:
  administering to a subject in need of such reduction of serum cholesterol, serum triglycerides, and/or atherosclerotic plaque an effective amount of a $5HT_3R$ antagonist or pharmaceutically-acceptable salt thereof.

18. The method of claim 17, wherein the subject has been identified as having nicotine-induced cardiovascular risk and/or the subject has a history of nicotine use.

19. The method of claim 17, wherein the subject is identified as having or being at risk of aneurysm.

20. The method of claim 17, wherein $5HT_3R$ antagonist is selected from the group consisting of: tropisetron, dolasetron, granisetron, ondansetron, palonosetron, and ramosetron.

* * * * *